(12) United States Patent
O'Brien et al.

(10) Patent No.: US 7,022,821 B1
(45) Date of Patent: Apr. 4, 2006

(54) ANTIBODY KIT FOR THE DETECTION OF TADG-15 PROTEIN

(76) Inventors: Timothy J. O'Brien, 2610 N. Pierce, Little Rock, AR (US) 72207; Hirotoshi Tanimoto, Nakabu-cho 1-5-53-401, Marugame, Kagawa 763-0033 (JP)

( * ) Notice: Subject to any disclaimer, the term of this patent is extended or adjusted under 35 U.S.C. 154(b) by 0 days.

(21) Appl. No.: 09/421,213

(22) Filed: Oct. 20, 1999

Related U.S. Application Data

(63) Continuation-in-part of application No. 09/027,337, filed on Feb. 20, 1998, now Pat. No. 5,972,616.

(51) Int. Cl.
*C07K 16/00* (2006.01)
*C07K 1/00* (2006.01)
*C07K 14/00* (2006.01)
*C07K 17/00* (2006.01)
*C12P 21/08* (2006.01)

(52) U.S. Cl. ............... 530/388.1; 530/350; 530/385; 530/386; 530/387.1; 530/387.9; 530/388.8; 530/388.85; 530/388.15; 530/389.1; 530/300

(58) Field of Classification Search ............. 530/350, 530/385, 386, 387.1, 387.9, 388.1, 388.15, 530/389.1, 388.8, 388.85, 300
See application file for complete search history.

(56) References Cited

U.S. PATENT DOCUMENTS 5,972,616 A  10/1999  O'Brien .................... 435/6

FOREIGN PATENT DOCUMENTS

JP      09149790 A  *  6/1997

OTHER PUBLICATIONS

Amino acid database, Accession #W22987, 1997.*
Lerner, Tapping the immunological repertoire to produce antibodies of predetermined specificity. Nature 229:592-596, 1982.*
Lin et al. Molecular cloning of cDNA for matriptase, a matrix-degrading serine protease with trypsin-like activity. The Journal of Biological Chemistry 274(26):18231-18236, Jun. 25, 1999.*
Database alignment, sequence comparison between Applicants' SEQ ID No.: 2 and Lin's sequence, 2001.*
Roitt, Ivan M. et al. Immunology, Third Edition, pp. 6.4 and 6.5, 1993. Publisher Mosby.*
English translation of Japanese document, J0149790-A, Jun. 1997.*
Harlow and Lane. Antibodies, A Laboratory Manual, pp. 319, 321-325 and 340-352, 1988.*

* cited by examiner

*Primary Examiner*—Alana M. Harris
(74) *Attorney, Agent, or Firm*—Benjamin Aaron Alder

(57) ABSTRACT

The present invention provides DNA encoding a TADG-15 protein as well as a TADG-15 protein. Also provided is a vector capable of expressing the DNA of the present invention adapted for expression in a recombinant cell and regulatory elements necessary for expression of the DNA in the cell. The present invention further provides for methods of inhibiting TADG-15 expression and/or protease activity, methods of detecting TADG-15 mRNA and/or protein and methods of screening for TADG-15 inhibitors. Additionally, the present invention provides for cell-specific targeting via TADG-15 and methods of vaccinating an individual against TADG-15. The instant invention also includes a kit containing antibodies for the detection of TADG-15 protein. The methods described are useful in the diagnosis, treatment and prevention of cancer, particularly breast and ovarian cancer.

6 Claims, 21 Drawing Sheets

```
Heps    RIVGGRDTSL GRWPWQVSL. ....RYDG.A HLCGGSLLSG DWVLTAAHCF PE....RNRV LSRWRVFAGA VAQASPHGLQ
Tadg15  RVVGGTDADE GEWPWQVSL. ....HALGQG HICGASLISP HWLVSAAHCY IDDRGFRYSD PTQWTAFLGL HDQSQRSAPG
Scce    KIIDGAPCAR GSHPWQVAL. ....LSGNQL H.CGGVLVNE RWVLTAAHC. ........K MNEYTVHLGS DTLG..DR.R
Try     KIVGGYNCEE NSVPYQVSL. ....NSGYHF ..CGGSLINE QWVVSAGHC. ........Y KSRIQVRLGE HNIEVLEG.N
Chymb   RIVNGEDAVP GSWPWQVSL. ....QDKTGF HFCGGSLISE DWVVTAAHC. ........GV RTSDVVVAGE FDQGSDEE.N
Fac7    RIVGGKVCPK GECPWQVLL. ....LVNG.A QLCGGTLINT IWVVSAAHCF DKIKNWRNLI .....AVLGE HDLSEHDGDE
Tpa     RIKGGLFADI ASHPWQAAIF AKHRRSPGER FLCGGILISS CWILSAAHCF QERFPPHHL. ....TVILGR .TYRVVFGEE Heps    LGVQAVVYHG GYLPFRDPNS EENSNDIALV HLSS.PLPLT EYIQPVCLPA ...AGQALVD GKICTVTGWG NTQYYGCQ.A
Tadg15  VQERRLKRII SHPFFNDFTF D...YDIALL ELEK.PAEYS SHVRPICLPD ...ASHVFPA GKAIHVTGWG HTQYGGTG.A
Scce    AQRIKASKSF RHPGYSTQT. ..HVNDLMLV KLNS.QARLS SHVKKVRLPS ...RCE..PP GTTCTVSGWG TTTSPDVTFP
Try     EQFINAAKII RHPQYDRKT. ..LNNDIMLI KLSS.RAVIN ARVSTISLPT ...APP..AT GTKCLISGWG NTASSGADYP
Chymb   IQVLKIAKVF KNPKFSILT. ..VNNDITLL KLAT.PARFS QTVSAVCLPS ...ADDDFPA GTLCATTGWG KTKYNANKTP
Fac7    QSRRVAQVII P....STYVP GTTNHDIALL RLHQ.PVVLT DHVVPLCLPE RTFSERTLAF VRFSLVSGWG QLLDRGATAL
Tpa     EQKFEVEKYI VHKEFDDDTY D...NDIALL QLKSDSSRCA QESSVVRTVC LPPADLQLPD WTECELSGYG KHEALSPFYS Heps    GVLQEARVPI ISNDVCNGAD FYGN..QIKP KMFCAGYPEG G......IDA CQGDSGGPFV CEDSISRTPR WRLCGIVSWG
Tadg15  LILQKGEIRV INQTTCE..N ELPQ..QITP RMMCVGFLSG G......VDS CQGDSGGPL. ...SSVEADGR IFQAGVVSWG
Scce    SDLMCVDVKL ISPQDCTKV. .YKD..LLEN SMLCAGIPDS K......KNA CNGDSGGPLV C....R.... GTLQGLVSWG
Try     DELQCLDAPV LSQAKCEAS. .YPG..KITS NMFCVGFLEG G......KITS NMFCVGFLEG G......VSS CMGDSGGPLV C....QKDGA WTLVGIVSWG
Chymb   DKLQQAALPL LSNAECKKS. .WGR..RITD VMICAG..AS G......VSS CMGDSGGPLV C....QKDGA WTLVGIVSWG
Fac7    ELMVLNVPRL MTQDCLQQSR KVGDSPNITE YMFCAGYSDG S......KDS CKGDSGGP.. ..HATHYRGT WYLTGIVSWG
Tpa     ERLKEAHVRL YPSSRCTSQH LLNRT..VTD NMLCAGDTRS GGPQANLHDA CQGDSGGPLV CLN...!.DGR MTLVGIISWG Heps    T.GCALAQKP GVYTKVSDFR EWIFQAIKTH SEASGMVTQLA-- (SEQ ID NO.3)
Tadg15  D.GCAQRNKP GVYTRLPLFR DWIKENTGV- ---------- --A (SEQ ID NO.4)
Scce    TFPCGQPNDP GVYTQVCKFT KWINDTMKKH R--------- --A (SEQ ID NO.5)
Try     D.GCAQKNKP GVYTKVYNYV KWIKNTIAAN S--------- --A (SEQ ID NO.6)
Chymb   SDTCS.TSSP GVYARVTKLI PWVQKILAAN ---------- --A (SEQ ID NO.7)
Fac7    Q.GCATVGHF GVYTRVSQYI EWLQKLMRSE PRPGVLLRAP PP A (SEQ ID NO.7)
Tpa     .LGCGQKDVP GVYTKVTNYL DWIRDNMRP- ---------- --A (SEQ ID NO.8)
```

FIGURE 1

```
  1  TCAAGAGCGGGCCTCGGGGGTACCATGGGGAGCGATCGGGCCCGCAAGGGCGAGGGGCCCAAGGACTTCGGCGC       18
                            M  G  S  D  R  A  R  K  G  G  G  P  K  D  F  G  A
 76  GGGACTCAAGTACAACTCCCGGCACGAGAAAGTGAATGGCTTGGAGGAAGGCGTGGAGTTCCTGCCAGTCAACAA       43
      G  L  K  Y  N  S  R  H  E  K  V  N  G  L  E  E  G  V  E  F  L  P  V  N  N
151  CGTCAAGAAGGTGGAAAAGCATGGCCCGGGGCGCTGGGTGGTGCTGGCAGCCGTGCTGATCGGCCTCCTCTTGGT       68
      V  K  K  V  E  K  H  G  P  G  R  W  V  V  L  A  A  V  L  I  G  L  L  L  V
226  CTTGCTGGGGATCGGCTTCCTGGTGTGGCATTTGCAGTACCGGGACGTGCGTGTCCAGAAGGTCTTCAATGGCTA       93
      L  L  G  I  G  F  L  V  W  H  L  Q  Y  R  D  V  R  V  Q  K  V  F  N  G  Y
301  CATGAGGATCACAAATGAGAATTTTGTGGATGCCTACGAGAACTCCACTGAGTTTGTAAGCCTGGCCAG           118
      M  R  I  T  N  E  N  F  V  D  A  Y  E  N  S  T  E  F  V  S  L  A  S
376  CAAGGTGAAGACGCGTCAGCGGCAGCTGAAGCGCTGAACGGAGTCCCATTCCTGGGCCCTACCACAAGGAGTCGGCTGT       143
      K  V  K  D  A  L  K  L  L  Y  S  G  V  P  F  L  G  P  Y  H  K  E  S  A  V
451  GACGGCCTTCAGCGAGGGCAGCGTCATCGCCTACTACTGGTCTGAGTTCAGCATCCCGCAGCACCTGGTGGAGGA       168
      T  A  F  S  E  G  S  V  I  A  Y  Y  W  S  E  F  S  I  P  Q  H  L  V  E  E
526  GGCCGAGCGCGTCATGGCCGAGGAGCGCGTAGTCATGCTCCCTCCGCGCGCTCGAAGTCCTTTGTGGT          193
      A  E  R  V  M  A  E  E  R  V  M  L  P  P  R  A  R  S  L  K  S  F  V  V
601  CACCTCAGTGGTGGCCTTTCCCCACGGACTCCAAAACAGTACAGAGGACCCAGACGCCCTTCCCTGACAGCCCTCCGCT       218
      T  S  V  V  A  F  P  T  D  S  K  T  V  Q  R  T  Q  D  N  S  C  S  F  G  L
676  GCACGCCCGGGTGTGGAGCTGATGCGCGGCACCACGCCCGGTCGCCCTGACAGCCCCTACCCCGCTCATGCCCG       243
      H  A  R  G  V  E  L  M  R  G  T  T  P  G  R  P  D  S  P  Y  P  A  H  A  R
```

Fig. 2A

```
 751 CTGCCAGTGGGCCCTGCGGGGGGACGCCGACTCAGTGCTGAGCCTCACCTTCCGCAGCTTTGACCTTGCGTCCTG  268
       L  P  V  G  P  C  G  G  D  A  D  S  V  L  S  L  T  F  R  S  F  D  L  A  S  C
       C  Q  W  A  L  R  G  D  A  D  S  V  L  S  L  T  F  R  S  F  D  L  A  S  C
 826 CGACGAGCGCGGCAGCGACCTGGTGTACAACACCCTGAGCCCCATGGAGCCCCACGCCCTGGTGCAGTT        293
       D  E  R  G  S  D  L  V  Y  N  T  L  S  P  M  E  P  H  A  L  V  Q  L
 901 GTGTGGCACCTACCCTCCCTCCTACAACCTGACCTTCCACAGCAGTCAGAACGTCCTCATCACACTGATAAC    318
       C  G  T  Y  P  P  S  Y  N  L  T  F  H  S  S  Q  N  V  L  I  T  L  I  T
 976 CAACACTGAGGCGGCCATCCCGGCTTTGAGGCCACTTCTTCCAGTGCCTAGGATGAGCAGCTGTGGAGCCG     343
       N  T  E  A  A  I  P  A  L  R  P  L  L  P  V  P  R  M  S  S  C  G  G  R
1051 CTTACGTAAAGCCCAGGGACATTCAACAGCCACTACCCAGCCACTGGCTTTCAAATTCTTCTACCTGCTGGAGCCCGGCGTGCC  368
       L  R  K  A  Q  G  T  F  N  S  P  Y  Y  P  G  H  Y  P  P  N  I  D  C  T  W
1126 GAACATTGAGGTGCCCAACAACCAGCATGTGAAGGTCAGCTTCAAATTCTTCTACCTGCTGGAGCCCGGCGTGCC  393
       N  I  E  V  P  N  N  Q  H  V  K  V  S  F  K  F  F  Y  L  L  E  P  G  V  P
1201 TGCGGGCACTTGCCCCAAGGACTACGTGGAGATCAATGGGGAGAAATACTGCGGGGAGAGGTCCCAGTTCGTCGT  418
       A  G  T  C  P  K  D  Y  V  E  I  N  G  E  K  Y  C  G  E  R  S  Q  F  V  V
1276 CACCGGCGACAACAAGAATCACAGTTCGCTTCCACTCAGATCAGTCTACAGTCCTACACCGGCTTCTTAGCTGA     443
       T  S  N  K  I  T  V  R  F  H  S  D  Q  S  Y  T  D  T  G  F  L  A  E
1351 ATACCCTCTCCTACGACTCCAGTGACCCATGCCCTGGCCAGTTCACGTGCCGCCGGTGTATCCGGAAGGA        468
       Y  L  S  Y  D  S  S  D  P  C  P  G  Q  F  T  C  R  T  G  R  C  I  R  K  E
1426 GCTGCGCTGTGATGGCTGGGCCGACTGCACTGACCACAGCGATGAGCTCAACTGCAGTTGCGACGCCGCCACCA   493
       L  R  C  D  G  W  A  D  C  T  D  H  S  D  E  L  N  C  S  C  D  A  G  H  Q
```

Fig. 2B

```
1501  GTTCACGTGCAAGAACAAGTTCTGCAAGCCCCTCTTCTGGGTCTGCGACAGTGAACGACTGCGGAGACAACAG     518
       F  T  C  K  N  K  F  C  K  P  L  F  W  V  C  D  S  V  N  D  C  G  D  N  S

1576  CGACGAGCAGGGGTGCAGTTGTCCGGCCCAGACCTTCCGGGGGACGGTCTGGGGACGTCCGACGAGGTCCGACGAGGTCCTGAAAAGCCAGCA     543
       D  E  Q  G  C  S  C  P  A  Q  T  F  R  C  S  N  G  K  C  L  S  K  S  Q  Q

1651  GTGCAATGGGAAGGACGACTGTGGGGACGGTCCGACGAGGTCCTGCCCCAAGGTGAACGTCGTCACTTGTAC     568
       C  N  G  K  D  D  C  G  D  G  S  D  E  A  S  C  P  K  V  N  V  V  T  C  T

1726  CAAACACACCTACCGCTGCCTCAATGGGCTCTGCTTGAGCAAGGCAACCCTGAGTGTGACGGGAAGGAGGACTG     593
       K  H  T  Y  R  C  L  N  G  L  C  L  S  K  G  N  P  E  C  D  G  K  E  D  C

1801  TAGCGACGGCTCAGATGAGAAGGACTGCGACTGTGGGCTCATTCACGAGACAGGCTCGTGTTGTGGGGG     618
       S  D  G  S  D  E  K  D  C  D  C  G  L  R  S  F  T  R  Q  A  R  V  G  G

1876  CACGGATGCGGATGAGGGCGAGTGGCCCTGGCAGTAAGCCTGCACACTGCTACATGGACACAGAGATTCAGTACTCAGA     643
       T  D  A  D  E  G  E  W  P  W  Q  V  S  L  H  A  L  G  Q  G  H  I  C  G  A

1951  TTCCCCTCATCTCTCCCAACTGGCTGGTCTCTGCCGCACAGCCAGCGACCAGAGCCAGCCAGGAGGCGCAG     668
       S  L  I  S  P  N  W  L  V  S  A  A  H  C  Y  I  D  D  R  G  F  R  Y  S  D

2026  CCCCACGCAGTGGACGGCCTTGCACGACGACAGAGCCAGCGACCAGAGCCAGCCAGGGTGCAGGAGCGCAG     693
       P  T  Q  W  T  A  F  L  G  L  H  D  Q  S  Q  R  S  A  P  G  V  Q  E  R  R

2101  GCTCAAGCGCATCATCTCCACCCCTTTCTTCAATGACTTCACCTTCGACTATGACATCGCCTGCTGGAGCTGGA     718
       L  K  R  I  I  S  H  P  F  F  N  D  F  T  F  D  Y  D  I  A  L  L  E  L  E

2176  GAAACCGGCAGAGTACAGCTCCATGGTGCGGCCCATCTGCCTGCCCGACGCCTCCCATGTCTTCCCTGCCGGCAA     743
       K  P  A  E  Y  S  S  M  V  R  P  I  C  L  P  D  A  S  H  V  F  F  P  A  G  K
```

Fig. 2C

```
2251 GGCCATCTGGGTCACGGGCTGGGACACACCCAGTATGGAGGCACTGGCGCGCTGATCCTGCAAAAGGGTGAGAT
      A  I  W  V  T  G  W  G  H  T  Q  Y  G  G  T  G  A  L  I  L  Q  K  G  E  I   768
2326 CCGCGTCATCAACCAGACCACCTGCGAGAACCTCCTGCCGCAGATCACGCCGCGCATGATGTGCGTGGGCTT
      R  V  I  N  Q  T  T  C  E  N  L  L  P  Q  I  T  P  R  M  M  C  V  G  F   793
2401 CCTCAGCGGCGGCGTGGACTCCTGCCAGGGTGATTCCGGGGACCCCTGTCCAGCGTGGAGGCGATGGCGGAT
      L  S  G  G  V  D  S  C  Q  G  D  S  G  G  P  L  S  S  V  E  A  D  G  R  I   818
2476 CTTCCAGGCCTGCTGCTCGTGGGGATGGGGACGGCTGCGCAGAGAACAAGCCAGGCGTGTACACAAGGCTCCC
      F  Q  A  F  C  C  S  W  G  D  G  C  A  Q  R  N  K  P  G  V  Y  T  R  L  P   843
2551 TCTGTTTCGGGACTGGATCAAAGAGAACACTGGGGTATAGGGGCCCCAAATGTGTACACCTGCGGGGG
      L  F  R  D  W  I  K  E  N  T  G  V            (SEQ ID NO: 2)           855
2626 CCACCCATCGTCCACCCCAGTGTGCACGCTGCAGGCTGACTGCACCAGCGCCCCCAGAA
2701 CATACACTGTGAACTGTCAATCTCCAGGGCTCCAAATCTGCCTAGAAAATCTGCTTCCTCAGCCTCCAAAGTGG
2776 AGCTGGGAGGTAGAAGGGAGGACACTGGCCGAGGCGCGTTGTTCTACTGACCCAACTGGGGCAAAGTTTGAAGACACAGCCT
2851 CCCCCGCCAGCCCCAAGCCTCCTCAGTGGTGTATATCTGCCGATCCTGGGCCCTTGGGCCCACGCTCT
2926 CGGAGCTTCGGAGCCTCCAGCCTCAGTGAAGTGTTGGGCTGAAGGTGGTTGGGGGCCCTTGGGCCACGCTCT
3001 TGAGGAAGCCCAGGCTGCTCGGAGGACCCTGAGACTGAAATTGTTTACCAGCTCCCAGGG
3076 TGGACTTCAGTGTGTGTATTGTGTAAATGGTAAACAATTTATTTCTTTTTAAAAAAAAAAAAAAAAAAA
                                                  (SEQ ID NO: 1)
```

―――― : KOZAK'S CONSENSUS SEQUENCE
===== : TRANSMEMBRANE DOMAIN
■ : CONSERVED AMINO ACIDS OF CATALYTIC TRIAD H, D, S

Fig. 2D

```
  1  MGSDRARKGG GGPKDFGAGL KYNSRHEKVN GLEEGVEFLP VNNVKKVEKH       1
 51  GPGRWVLAA VLIGLLLVLL GIGFLVWHLQ YRDVRVQKVF NGYMRITNEN        2
101  FVDAYENSNS TEFVSLASKV KDALKLLYSG VPFLGPYHKE SAVTAFSEGS
151  VIAYWSEFS IPQHLVEEAE RVMAEERVVM LPPRARSLKS FVVTSVVAFP
201  TDSKTVQRTQ DNSCSFGLHA RGVELMRFTT PGFPDSPYPA HARCQWALRG        3
251  DADSVLSLTF RSFDLASCDE RGSDLVTVYN TLSPMEPHAL VQLCGTYPPS
301  YNLTFHSSQN VLLITLITNT ERRHPGFEAT FFQLPRMSSC GGRLRKAQGT
351  ENSPYYPGHY PPNIDCTWNI EVPNNQHVKV SFKFFYLLEP GVPAGTCPKD
401  YVEINGEKYC GERSQFVVTS NSNKITVRFH SDQSYTDTGF LAEYLSYDSS
451  DPCPGQFTCR TGRCIRKELR CDGWADCTDH SDELNCSCDA GHQFTCKNKF        4
501  CKPLFWVCDS VNDCGDNSDE QGCSCPAQTF RCSNGKCLSK SQQCNGKDDC
551  GDCSDEASCP KVNVVTCTKH TYRCLNGLCL SKGNPECDGK EDCSDCSDEK
601  DCDCGLRSFT RQARVVGGTD ADEGEWPWQV SLHALGQGHI CGASLISPNW        5
651  LVSAACYID DRGFRYSDPT QWTAFLGLHD QSQRSAPGVQ ERRLKRIISH
701  PFFNDFTFDY DIALLELEKP AEYSSMVRPI CLPDASHVFP AGKAIWVTGW
751  GHTQYGGTGA LILQKGEIRV INQTTCENLL PQQITPRMMC VGFLSGGVDS
801  CQGDSGGPLS SVEADGRIFQ AGVVSWGDGC AQRNKPGVYT RLPLFRDWIK
851  ENTGV       SEQ ID NO:2

*     : Conserved cysteine residue                            1. Cytoplasmic domain
NXT   : Possible N-linked glycosylation site                  2. Transmembrane domain
SDE   : Conserved SDE motif                                   3. CUB repeat
▼     : Potential cleavage site                               4. Ligand-binding repeat (class A motif)
○     : Conserved amino acids of catalytic triad H, D, S         of LDL receptor like domain
                                                              5. Serine protease
```

FIGURE 3

```
hTADG15   MGSDRARKGG GGPKDFGAGL KYNSRHEKVN GLEEGVEELP VNNVKKVEKH   50
mEpithin  ---N-G--A- ------SQ-- --D---L-NM- -F-------- A--A-----R hTADG15   GPGRWVLAA VLIGLLIVLL GIGFLVWHLQ YRDVRVQKVF NGYMRITNEN   100
mEpithin  --R-----V- --FSF--LS- MA-L-----FH --N------- --HL------I hTADG15   FVDAYENSNS TEFVSLASKV KDALKLLYSG VPFLGPYHKE SAVTAFSEGS   150
mEpithin  -L-------T ------Q--- --E------NE --V------K ---------- hTADG15   VIAYYWSEFS IPQHLVEEAE RVMAEERVVM LPPRARSLKS FVVTSVVAFP   200
mEpithin  ---------- --P--A---VD -A---V----T ------A--- --L------- hTADG15   TDSKTVQRTQ DNSCSFGLHA RGVELMRFTT PGFPDSPYPA HARCQWALRG   250
mEpithin  I-PRML---- ---------- ------A---- H-AAVT---- -----N---- ---V------ hTADG15   DADSVLSLTE RSFDLASCDE RGSDLVTVYN TLSPMEPHAL VQLCGTYPPS   300
mEpithin  ---------- ---V-P---- H--------D S---------- -R-----FS-- hTADG15   YNLTEHSSQN VLLITLITNT ERRHPGFEAT FFQLPRMSSC GGRLRKAQGT   350
mEpithin  ---------- -F-V------ G-----L--- ------K---- --V-SDT--- hTADG15   FNSPYYPGHY PPNIDCTWNI EVPNNQHVKV SEKFFYLLEP GVPAGTCPKD   400
mEpithin  -S-------- -----N---- K----RN--- R---L---VD- N--V-S-T-- hTADG15   YVEINGEKYC GERSQFVVTS NSNKITVREH SDQSYTDTGF LAEYLSYDSS   450
mEpithin  ---------GS -------S- ---S----H- ------H--- --------N
```

Fig. 11A

```
hTADG15   DPCPGQFTCR TGRCIRKELR CDGWADCTDH SDELNCSCDA GHQFTCKNKF  500
mEpithin  -----M-M-K ---------- ---------- ---RY-R-N- T-----Q--- hTADG15   CKPLFWVCDS VNDCGDNSDE QGCSCPAQTF RCSNGKCLSK SQQCNGKDDC  550
mEpithin  ---------- --------G- ---E------ -GS-K----- --K-----N- hTADG15   GDGSDEASCP KVNVVTCTKH TYRCLNGLCL SKGNPECDGK EDCSDGSDEK  600
mEpithin  ---------- -D S-----Y ---------- ----Q----- T--------- hTADG15   DCDCGLRSFT RQARVVGGTD ADEGEWPWQV SLHALGQGHI CGASLISPNW  650
mEpithin  N--------- ---K------ ---------N ---------- -------L--D- hTADG15   LVSAAHCYID DRGFRYSDPT QWTAFLGLHD QSQRSAPGVQ ERRLKRIISH  700
mEpithin  --------- -FQ--KN-K--Y- M---------L ----K---S-- -LK-----T-- hTADG15   PFFNDFTEDY DIALLELEKP AEYSSMVRPI CLPDASHVFP AGKAIWTGW  750
mEpithin  -S-------- ---------S V---TV---- -----T---- --------- hTADG15   GHTQYGGTGA LILQKGEIRV INQTTCENLL PQQITPRMMC VGFLSGGVDS  800
mEpithin  ---KE----- ---------- ---------- -----D-M-- ---------- hTADG15   CQGDSGGPLS SVEADGRIFQ AGVVSWGDGC AQRNKPGVYT RLPLFRDWIK  850
mEpithin  ---------- ---A-K---M- ------E--- ---------- ---CSSGLDQ hTADG15   ENTGV*                                                  900
mEpithin  RAHWGIAAWT DSRPQTPTGM PDMHITWIQER NTDDIYAVAS PPQHNPDCEL hTADG15    SEQ ID NO: 2                                           902
mEpithin HP SEQ ID NO: 10

Fig. 11B
```

```
TADG15:    TCAAGAGCGGCCTCGGGGTACCATGGGAGCGGATCGGGCCCGCAAGGGCGGAGGGCCCGAAGGACTTCGGCGGGACT  81

SNC19:     ................................................................................

CAAGTACACAACTCCCGGCACGAGAAAGTGAATGGCTTGGAGGAAGGCGTGAGTTCCTGCCAGTCAACAACGTCAAGAGAAGTGGAAAAGCATGGCCCGGGG
82

CGCTGGGTGGTGCTGGCCAGCCGTGCTGATCGGCCTCCTCTCTTGGTCTTGTGTTGGGATCGGCTGTGCTGGTGTGGCATTTGCAGTACCGGGACGTGCTGTCC  281
182         ||||||||||||||||||||||||||||||||||||||||||||||||||||||||||||||||||||||||||||||||||||||||||||||||||
1          CGCTGGGTGGTGCTGGCCAGCCGTGCTGATCGGCCTCCTCTCTTGGTCTTGTGTCTTGGGATCGGCTGTGCTGGTGTGGCATTTGCAGTACCGGGACGTGCTGTCC  100

AGAAGGTCTTCAATGGCTACATGAGGATCACAAATGAGAATTTGTGGATGCCTACGAGAACTCCAACTGAGTTTGTAAGCCTGGCCAGCAAGGT  381
282         ||||||||||||||||||||||||||||||||||||||||||||||||||||||||||||||||||||||||||||||||||||||||||||||||||
101        AGAAGGTCTTCAATGGCTACATGAGGATCACAAATGAGAATTTGTGGATGCCTACGAGAACTCCAACTGAGTTTGTAAGCCTGGCCAGCAAGGT  200

GAAGGACGCGCTGAAGCTGCTGTACAGCGGAGTCCCATTCCTGGGCCCCTACCACCACAAGGAGTCGGCTGTGACGGCCTTCAGCGAGGGCAGCGTCATCGCC  481
382         ||||||||||||||||||||||||||||||||||||||||||||||||||||||||||||||||||||||||||||||||||||||||||||||||||
201        GAAGGACGCGCTGAAGCTGCTGTACAGCGGAGTCCCATTCCTGGGCCCCTACCACCACAAGGAGTCGGCTGTGACGGCCTTCAGCGAGGGCAGCGTCATCGCC  300

TACTACTGGTCTGAGTTCAGCATCCCCGCAGCCTGGTGGAGGAGCCGAGCGCGTCATGCCGAGGAGCCGAGCGCGTAGTCATGCCGAGGAGCCGAGCGCGCT  581
482         ||||||||||||||||||||||||||||||||||||||||||||||||||||||||||||||||||||||||||||||||||||||||| |||||||||||
301        TACTACTGGTCTGAGTTCAGCATCCCCGCAGCCTGGTGGAGGAGCCGAGCGCGTCATGGCC AGGAGCCGAGCGCGTAGTCATGCCGAGGAGCCGAGCGCGCT  399

CCCTGAAGTCCTTTGTGGTCACCTCAGTGGTGGCTTTCCCCACGGACTCCAAAACAGTACAGACTCCAGGACAACAGCTGCAGCTTTGGCCTGCACGC  681
582         ||||||||||||||||||||||||||||||||||||||||||||||||||||||||||||||||||||||||||||||||||||||||||||||||
400        CCCTGAAGTCCTTTGTGGTCACCTCAGTGGTGGCTTTCCCCACGGACTCCAAAACAGTACAGACTCCAGGACAACAGCTGCAGCTTTGCCTGCACG  498
```

```
1375  CCCATGCCCGGGGCAGTTCACGTGCCGCACGGGCGGCTGTGTATCCGGAAGGAGCTGCGCTGTGATGGCTGGCCGACTGCACCGACCACAGCGATGAGCTC  1474
      ||||||||||||||||||||||||||||||||||||||||||||||||||||||||||||||||||||||||||||||||||||||||||||||||||
1182  CCCATGCCCGGGGCAGTTCACGTGCCGCACGGGCGGCTGTGTATCCGGAAGGAGCTGCGCTGTGATGGCTGGCCGACTGCACCGACCACAGCGATGAGCTC  1290

1475  AACTGCAGTTGCGACGCGGCCACCAGTTCACGTGCAAGAACAAGTTCTGCAAGCCCCTCTTCTGGGTCTGCGACAGTGTGAACGACTGCGGAGACAACA    1574
      |||.||.||||||||||||||||||||||||||||||||||||       ||||||||||||||||||||||||||||||||||||||||||||||
1281  AACTGCAGTTGCGACGCGGCCACCAGTTCACGTGCAAGAGAGCAAGTTCTGCAAG...CTCTTCTGGGTCTGCGACAGTGTGAACGACTGCGGAGACAACA  1377

1575  GCGACGAGCAGGGGTGCAGTTGTCCGG.CCCAGACCTTCAGTGTTCCAATGGAAGTGCCTCTCGAAAAGCCAGCAGTGCAATGGGAAGGACGACTGTG    1673
      |||||||||||||||||||||||||||  |||||||||||||||||||||||||||||||||||||||||||||||||||||||||||||||||||
1378  GCGACGAGCAGGGGTTGCATTTGTCCGACCCCAGACCTTCAGTGTGTTCCAATGGAAGTGCCTCTCGAAAAGCCAGCAGTGCAATGGGAAGGACGACTGTG  1477

1674  GGGACGGGTCCGACGAGGCCTCCTGCCCCAAGTGAACGTCGTCAAAACACACCTACCGCTGCCTCAATGGGCTCTCTGCTTGAGCAAGGGCAA        1773
      |||||||||||||||||||||||||||||||||||||||||||||||||||||||||||||||||||||||||||||||||||||||||
1478  GGGACGGGTCCGACGAGGCCTCCTGCCCCAAGTGAACGTCGTCAAAACACACCTACCGCTGCCTCAATGGGCTCTCTGCTTGAGCAAGGGCAA        1577

1774  CCCTGAGTGTGACGGGAAGGAGGACTGTAGCGACGGCTGTGGGCGGTCATTCACGAGACAGGCTCGTGTTGTTGG                            1873
      |||||||||||||||||||||||||||||||||||||||||||||||||||||||||||||||||||||||||||
1578  CCCTGAGTGTGACGGGAAGGAGGACTGTAGCGACGGCTGTGGGCGGTCATTCACGAGACAGGCTCGTGTTGTTGGG                           1677

1874  GGCACGGATGCGGATGAGGGCGAGTGGCCCTGGCAGGTAAGCCTGCATGCTCTGGGCGCTTCCCTCATCTCTCCCAACTGGC                     1973
      ||||||||||||||||||||||||||||||||||||||||||||||||||||||||||||||||||||||||||||||
1678  GGCACGGATGCGGATGAGGGCGAGTGGCCCTGGCAGGGCCCTGGCAGTAAGCCTGCATGCTCTGGGCGTGCTTCCCTCATCTCTCCCAACTGGC         1777

1974  TGGTCTCTGCCGCACACTGCTACATCGATGACAGAGGATTCAGTGTACTCAGAGACCCCACGCA..GGACGGCCTTCCTGGCTTGCACGACCAGAGCCAGCG  2073
      ||||||||||||||||||||||||||||||||||||||||||||||||||||||||||||||  ||||||||||||||||||||||||||||||||||||
1778  TGGTCTCTGCCGCACACTGCTACATCGATGACAGAGGATTCAGTACTCAGACCCCACGCA...GGACGGCCTTCCTGGCTTGCACGACCAGAGCCAGCG   1875
```

```
2771 AGTGGAGCTGGGA.GGTAGAAGGGGAGG.ACACTGTGGTGTTCTACTGACCCAACTGGGGCAAAGTTTGAAGACACAGCCTCCCCCGCCAGCCCCAAGC 2868
     |||||||||||||  |||||||||||||| |||||||||||||||||||||||||||||||| ||||| |||||       ||| |||||  ||||
2568 AGTGGAGCTGGGAGGGTAGAAGGGGAGAAGGGGAGAACACTGTGGTTCTACTGACCCAACTGGGG..CAAGGTTTGAAG.CACAG....CTCCGGCAGCCC..AAG 2658

2869 TGGGCCGAGGCGCGTTTGTGTATATCTGCCTCCCCCGTCTGTAAGGAGCAGCGGGAACGGAGCCTCCTCAGTGAAGGTGGTGGGCTGCCGG 2968
     |||||   ||||||||||  |||||||| ||| ||    |||| ||| |||     |||   ||   ||  ||||| |||
2659 TGGGCGAGGACGCGTTTGTGCATA.CTGCC..CTGCTCTATACACGGAAGACCTGGA........TCTCTAGTGA......GTGTGACTGCCGG 2735

2969 ATCTGGGCTGTGTGGGGCCCCTTGGGCCACGCTCTTGAGGAAGCCCAGGCTCGGAGGACCCCTGGAAAACAGAACGGGTCTGAGACTGAAATTGTTTTACCAGCT 3068
     |||||||   ||||||||||||| |||||||  |||||||||||||||||||||||||||||||||||||||||||||||||||||| ||||||||||||||
2736 ATCTGG...CTGTGGTCCTTGGCCACGCTTCTTGAGGAAGCCCAGGCTCGGAGGACCCCTGGAAAACAGAACGGGTCTGAGACTGAAAATGGTTTACCAGCT 2832

3069 CCCAGGGTGGACTTCAGTGTGTGTATTTGTGTAAATGGGTAAAACAATTTATTTCTTTTTAAAAAAAAAAAAAAAAA 3147 (SEQ ID NO: 1)
     ||||||  ||||||||||||||||| ||||||||||||||| |||||||| |||||||||||||||||||||||
2833 CCCAGG..TGACTTCAGTGTGTGTA.TTGTGTAAATGAGTAAAACATTTTATTTCTTTTTAAAAAAAAAAAA......... 2900 (SEQ ID NO: 9)
```

Fig. 12E

SEQUENCE LISTING

<160> NUMBER OF SEQ ID NOS: 20

<210> SEQ ID NO 1
<211> LENGTH: 3294
<212> TYPE: DNA
<213> ORGANISM: Nicotiana tabacum
<220> FEATURE:
<221> NAME/KEY: unsure
<222> LOCATION: location (1274), (1418), (1585), (1712), (2952), (2953)
<223> OTHER INFORMATION: n is any nucleotide

<400> SEQUENCE: 1

```
tcgagccatt catgttcagc ccattctgga aagttgctac aaccattcct tctgatacat      60
tcggtaaggt catccttact ctgttgaatc gagcgaggaa gtccctcaat ccctctccga     120
gtgattgttt gatggcaaat atatcgttca ctcttgcctc cgcgttttta gccccaacat     180
gggccattat gaacttgtcg gccatctctt cgaatatttc aatggagcgc gcgggcagct     240
gtgaatacca agtcaatgct cctccggtaa gggtctcgcc gaacattttc aacaagatgg     300
aggagacttg ttctttggag agatcattgc cctttaccgc agtgacataa tgattacatg     360
atcttcgggg tcggtcgtac catcataaat tttcagataa ggtggcatct tgaacgtctt     420
gggtatggca tatgggcgg cttcatcact gtagggttgc tcgactaacc gaccagcgtc     480
tcttttggga aatattttg gggcacccgg tattttatcg actctttctt ggtgttctct     540
catttgatcc cgaagcattt tattttcgtt ttccatttct tccatttcct tcagaatggc     600
cgtgagggtg tcattacctg cattattaat attgtgagtg atacctgtta ctgaaggggg     660
agggtcgtgc tgtttggtca ttgctggtgc aatgcaagtc cttgcatttt ctctaaatac     720
ctcctgagtg ggtttgttga ggatgccggt cagcatattt gtcagccaag cttcgagtag     780
cttcttcacc gctggtggcg cctcttccgt tgtggacgtg gaagctcctt taccgcggga     840
tgttgcgata ctgctgtgag ggaggggtga tccacttcgt cggggagagg tgttaggcgt     900
tatgccttcg ccttctattt cggagacctc attgatggtg tttaagaggt tggtagtgag     960
attggccact gccttcatcc tttcttctcc cttacctgcc atgtcagatc tgggtgtaca    1020
aggaagtagg agcttctctt cttctttttt gtgaattgtg ccagttatag atctaaaaga    1080
aactaaagtt ttaactagac tatcctcaca gacggcgcca aattgtttga ccaaaaaata    1140
tagacttttg attaaattaa ttaatattgt atgacaaagg attaaaccta gttaatgata    1200
ataacttcag atctataatc aattaacagc aatcacggtc atagcagcgt tgagagaaga    1260
ttaaatgtga tgtncattca atatttcaag atcattaatg atagggggaat atcaagcaat    1320 aaataacgat aaatggcatt aaagtaaata aggagaatga ttcacccaat attgaatgag    1380
gtggatgatt cttcttttg acaatgatga atgatggnca aatactagaa tgttgggacc    1440
```

-continued

| | |
|---|---|
| cttctcggat ctaatgaaaa aagtatggaa tagtagataa tcgaatctct ttagaaaggt | 1500 |
| agtgattgtc ttttatctag agagaaagtc tgcttttcaa agaatatttt tatcagagaa | 1560 |
| tattacatcc ccctctctcc ctatntcttt ttctatttat atgggacatt cctcaatcaa | 1620 |
| tcctaaaagt acatacacca agaatattca ataaaatatt tttttgaata ttctattata | 1680 |
| aaaactagct gttagcactc gacctcggtc gntattgact actcggttac gagccctgtc | 1740 |
| atttactaat cgacctcgat tacatcactt tctacgatac tgcttcatgt caaatcttaa | 1800 |
| tgaaagcaga ttttgaccca tacaataata tgacaaaatt gcttccaaag aaaacatggc | 1860 |
| tcttatagtg aaatatcgtt agactgttat agaaagatct gaatttattt ataagaatag | 1920 |
| tgttttttc ttttcttttc atatctaagg agtaaagcaa ccatgaatag aaaaggctta | 1980 |
| gtaactatat atcaaaggaa tggtgttttt tcttaaaata tggataaaaa tttgtgaata | 2040 |
| tagaagatta gatcaattaa caaaggttat ggtggagtgg taagcagagg cggacctatg | 2100 |
| tgttatagta agggtcacc cactactaga atccggtaa agatcgatca aaaaccgac | 2160 |
| caacattggt cggtaatggc caaaactga ccaaacgcg atcatttacg tgtgaacggt | 2220 |
| atttttatgg tcggaaagga ataccgacca aagttggtcg gaaattaccg accaactttg | 2280 |
| gtcggtcaat taaattcaaa aaaatattg taaaaaaaaa ccgaccaaag ttgatcggta | 2340 |
| ttttaattat gtaataaaaa gattcactat ctgggaatcg aaccgggtc tgtactatgg | 2400 |
| caagatacta ttctaccact agaccattgg ttcattttgt tttaagactg tcttttattt | 2460 |
| gatttatact ctttaattat attttgcac gaaaataacc gaccaaagtt ggtcgatttt | 2520 |
| attaaaagt aaaattactt accaagttg gtcgatttt ttaaatgatc cgccgaatta | 2580 |
| accgaccaat tttggtaggt tttttaata ttaattttta tttatttaa ttgaaaaact | 2640 |
| aaccaaagtt agtcggtttc ttgaaacata aatttcgcgg gactcaaaa tagtttcccg | 2700 |
| cattttgcg ccaaagaaaa ccgaccaaag ttggtcggtt tcgtaaaaaa aaaaaaaatt | 2760 |
| taaaaatat attttaaaaa accgaccaac tttagtcggt ttttggtcg attttttgac | 2820 |
| cgaccaaagt tggtcggtcg accttggtcg gttttgccg aatttctagt agtgaccgaa | 2880 |
| ccctgtaagc ttcgggagaa attttgtata tgtatatgtg tatatcctta aaatgattaa | 2940 |
| tttaagaac gnngcaccct gaatactaga agcctttagg ggcactagat gagcagaata | 3000 |
| acgtgttctc gtcgcgtaaa aatacttgga tccgcctatg atggtaagta cttcttcgtc | 3060 |
| cttaatcaga ggtttcgact tcgagctcca gatataaact atagactcgt ctttatagca | 3120 |
| cctttaata agactatgac ttcatctgat ttctctataa atactcctca agctttcggt | 3180 |
| tcttctccat tgttcagttt ctttctccac atcacagaag tgaaaacaaa acaagaagaa | 3240 |
| gaagaagaag aaaaataaag agtttctgtc aaattaagtc aatagggaa aatg | 3294 |

<210> SEQ ID NO 2
<211> LENGTH: 4312
<212> TYPE: DNA
<213> ORGANISM: Nicotiana tabacum

<400> SEQUENCE: 2

| | |
|---|---|
| tctagaatga cgccaccggc caggacgggg agtatgattt ccccgaatgt tcgttcaact | 60 |
| gcattgttaa aacctgttag cgtgatgcag cccggtacta tcttatcctc gagtttcatt | 120 |
| tgtgcaagta ctcgaggatg gacaattcac gggccactcc catcgtccac cataatgcgt | 180 |
| cttacatctg tatctaatat tcgtaaagtg ataacgaggg catcatagtg agggaaaacc | 240 |
| aaaccgtggt tatctgactt atcgaagatg atactttctt taagtttctc gtaccgttca | 300 |

-continued

```
tgagtgatta actgtttgag cttgtgggtt gtggcgaact ttacgttgtt gatcgaaacg    360
tcgtctccgc ccccgatgat aatgtgaatg gtgcgagtcg gtaagggtgg tttcggcggt    420
ccctggtgtt gttcacgtcc tcgagaaaag ttggtccttc ctcggtcaca caacaatatt    480
ttgaggtgtc cttgatgaag catgtccatg acctcttgtc ttagggcgat acaatcctca    540
gttttgtgac ctcgctcttg gtggaactcg cagagggcat ctgattttct agtgcttgga    600
tctgacctca tcttttgtgg ccactttact tttggtccga gcttcttcaa tgcatagact    660
atttctgagg gtgacacaca aaatttgtga gcggatagta aagagggcat acctctctcg    720
ttccggtgag tccctgtcct tggcctagat gggccctctt cgtagcggga gaggggcatg    780
atggcacttt tgacatatgg ttgatccatt tctcggttag atcatggagc tgcaagatct    840
ctcttggcat cattttgacg atccttcctg gtttcggctt gtaccgaggt caatcgatga    900
gttggcccat tcaggtcgtc ttcgtcggca cgggcctcag cacagtaggc gttgtgtatt    960
tcatcccaag tggttggagg atatttcata agttggttta acagttttct ggtcgccctc    1020
gagccattca tgttcagccc attctggaaa gttgctacaa ccattccttc tgatacattc    1080
ggtaaggtca tccttactct gttgaatcga gcgaggaagt ccctcaatcc ctctccgagt    1140
gattgtttga tggcaaatat atcgttcact cttgcctccg cgttttagc cccaacatgg     1200 gccattatga acttgtcggc catctcttcg aatatttcaa tggagcgcgc gggcagctgt    1260
gaataccaag tcaatgctcc tccggtaagg gtctcgccga acattttcaa caagatggag    1320
gagacttgtt ctttggagag atcattgccc tttaccgcag tgacataatg attacatgat    1380
cttcggggtc ggtcgtacca tcataaattt tcagataagg tggcatcttg aacgtcttgg    1440
gtatggcata tggggcggct tcatcactgt agggttgctc gactaaccga ccagcgtctc    1500
tttttggaaa tattttggg gcacccggta ttttatcgac tctttcttgg tgttctctca     1560
tttgatcccg aagcatttta ttttcgtttt ccatttcttc catttcttc agaatggccg     1620 tgagggtgtc attacctgca ttattaatat tgtgagtgat acctgttact gaaggggggag   1680 ggtcgtgctg tttggtcatt gctggtgcaa tgcaagtcct tgcattttct ctaaatacct    1740
cctgagtggg tttgttgagg atgccggtca gcatatttgt cagccaagct tcgagtagct    1800
tcttcaccgc tggtggcgcc tcttccgttg tggacgtgga agctccttta ccgcgggatg    1860
ttgcgatact gctgtgaggg agggtgatc cacttcgtcg gggagaggtg ttaggcgtta     1920
tgccttcgcc ttctatttcg gagacctcat tgatggtgtt taagaggttg gtagtgagat    1980
tggccactgc cttcatcctt tcttctccct tacctgccat gtcagatctg ggtgtacaag    2040
gaagtaggag cttctcttct tcttttttgt gaattgtgcc agttatagat ctaaagaaa     2100 ctaaagtttt aactagacta tcctcacaga cggcgccaaa ttgtttgacc aaaaaatata    2160 gactttgat taaattaatt aatattgtat gacaaaggat taaacctagt taatgataat     2220
aacttcagat ctataatcaa ttaacagcaa tcacggtcat agcagcgttg agagaagatt    2280
aaatgtgatg tycattcaat atttcaagat cattaatgat aggggaatat caagcaataa    2340
ataacgataa atggcattaa agtaaataag gagaatgatt cacccaatat tgaatgaggt    2400
ggatgattct tcttttgac aatgatgaat gatgggcaaa tactagaatg ttgggaccct     2460
tctcggatct aatgaaaaaa gtatggaata gtagataatc gaatctcttt agaaaggtag    2520
tgattgtctt ttatctagag agaaagtctg cttttcaaag aatatttta tcagagaata     2580 ttacatcccc ctctctcccct atctctttt ctatttatat gggacattcc tcaatcaatc    2640
ctaaaagtac atacaccaag aatattcaat aaaatatttt tttgaatatt ctattataaa    2700
```

-continued

```
aactagctgt tagcactcga cctcggtcgy tattgactac tcggttacga gccctgtcat   2760
ttactaatcg acctcgatta catcactttc tacgatactg cttcatgtca aatcttaatg   2820
aaagcagatt ttgacccata caataatatg acaaaattgc ttccaaagaa acatggctc    2880
ttatagtgaa atatcgttag actgttatag aaagatctga atttatttat aagaatagtg   2940
ttttttttctt ttcttttcat atctaaggag taaagcaacc atgaatagaa aaggcttagt  3000
aactatatat caaggaatg gtgttttttc tttaaatatg gataaaaatt tgtgaatata    3060
gaagattaga tcaattaaca aaggttatgg tggagtggta agcagaggcg gacctatgtg   3120
ttatagtaag gggtcaccca ctactagaaa tccggtaaag atcgatcaaa aaaccgacca   3180
acattggtcg gtaatggcca aaaactgacc aaaacgcgat catttacgtg tgaacggtat   3240
ttttatggtc ggaaaggaat accgaccaaa gttggtcgga aattaccgac caactttggt   3300
cggtcaatta aattcaaaaa aaatattgta aaaaaaaacc gaccaaagtt gatcggtatt   3360
ttaattatgt aataaaaaga ttcactatct gggaatcgaa ccgggtctg tactatggca    3420
agatactatt ctaccactag accattggtt catttgttt taagactgtc ttttatttga    3480
tttatactct ttaattatat ttttgcacga aaataaccga ccaaagttgg tcgatttat    3540
taaaagtaa aattacttac caaagttggt cgatttttt aaatgatccg ccgaattaac     3600
cgaccaattt tggtaggttt tttaatatt aatttttatt tattttaatt gaaaaactaa    3660
ccaaagttag tcggtttctt gaaacataaa tttcgcggga ctcaaaaata gtttcccgca   3720
tttttgcgcc aaagaaaacc gaccaaagtt ggtcggtttc gtaaaaaaaa aaaaaattta   3780
aaaaatatat tttaaaaaac cgaccaactt tagtcggttt tttggtcgat tttttgaccg   3840
accaaagttg gtcggtcgac cttggtcggt ttttgccgaa tttctagtag tgaccgaacc   3900
ctgtaagctt cgggagaaat tttgtatatg tatatgtgta tatccttaaa atgattaatt   3960
taaagaacgt ggcaccctga atactagaag cctttagggg cactagatga gcagaataac   4020
gtgttctcgt cgcgtaaaaa tacttggatc cgcctatgat ggtaagtact tcttcgtcct   4080
taatcagagg tttcgacttc gagctccaga tataaactat agactcgtct ttatagcacc   4140
ttttaataag actatgactt catctgattt ctctataaat actcctcaag ctttcggttc   4200
ttctccattg ttcagtttct ttctccacat cacagaagtg aaaacaaaac aagaagaaga   4260
agaagaagaa aaataaagag tttctgtcaa attaagtcca atagggaaaa tg           4312
```

<210> SEQ ID NO 3
<211> LENGTH: 2019
<212> TYPE: DNA
<213> ORGANISM: Lycopersicon esculentum cv. Moneymaker

<400> SEQUENCE: 3

```
cataatcaaa tgtgtggtct tatgtagaac taatatttgg taatattagg caagttgtta    60
tgtgacttat tttattcaaa aatataataa gaagttcaaa gagaagagta caagtaagta   120
agtaagcaga gacgaatcct ggatttaaag ggtctggcta tattaatgtt ttttttaattt  180
aagcattagc gattcgcctt gcaagtaatc gataggacaa aagttttacc ttactaattc   240
tattgaggca ccaaatccct atgaaaaagc atgtaaaata tgagaagacg aaagaattaa   300
ataggttata attattgtat aatttataac acactttatg ataatattac aaataagaat   360
atcgaatatt taattaatga cgaactataa aagcaaagaa ggaaggatga gcttccaaaa   420
acaatcgcaa atgaataaag atgcccaaaa tagagtaacc taacgaagtc gatacttcca   480
ttcataatca aatctgttca aaaacacttg atgggttatt tttaactttta agagatgtat  540
```

-continued

```
catatcgtct cttattattc ctttagggct attcgccgta ggaataaaat ttatatgatc      600
aaatttcacg ttatataaat aatgtgaaga aaaaacttat acttttcaag gtaacaagaa      660
atcatgtttt ttttacgcct tcgtggagac tacttcctcg taacaaaaaa ttaacatttt      720
aagtggcgac tctaaaaact cgtggccagt atattagtcg ccattaaaca ttatttttaa      780
tcatgagttc ttttcttttt taatctttt ttaaggtcaa atttaccact ttatcttatt      840
tatttaaatt gaaaatccc aaatttttgca ttattttttt gaattccttt ttttttttaca     900 cactcaaaaa gtcaaaacat taaaaaaacg aaatagcaaa ttaaatggca aaagacttgt      960
tgtaacaaaa aaaaaatagt aaaacagact cataaaaggt aacaataacc aacaaatcac     1020
acaaaattgt agataaatat tatgcaaaca ataaaaatt aataatccaa tccatttatt     1080
tattttttta aaaaaaacct aaattaactc tccatctttc aatcaaaaac aaactctacc     1140 cattttttc actataaata ctcttcataa ttttcatttg ttcttcattc ccatgtttct     1200
tttctcctta tccaaaaaaa aaaaaattaa aaaaaattat ttagattaaa tatcactatc     1260
tgtcaaagcc caatcattaa aataaaataa aaattatgga ttattcatct aataaaagtt     1320
ctcgttgggc tttgccagtt atcttagttt gcttttttgt aatttttatta tccaataatg    1380 ttgttttttgc ttctcataaa gttttattc acttgcaatc tcaaaatgcc gtaaatgttc     1440
atactgttca tcgaactggt tatcattttc agcccgaaaa acattggatc aatggtatgt     1500
ttattccttt ttttcgtctt tttttttatat atatatatat aataaaacga acatgttgtg    1560
tttagtctag atttaatact agtgattttt ttgacgctaa caaataatcg agtactcacc     1620
atttgtcaat agatacattg acatgtatta gtatgatttt cgtcttttt cgttgtttct     1680 aatattattt aatcttcact aattttttta tttttctttg aatgatgtct cttggtcaaa     1740
acatacaata gatcccaatg gtaagttaac tatattttg tatattttt aaatttattt      1800 tattcttatt atataatata gggaaaaaag gataaatata tccccgaact attataaata    1860
gtatgcacca gtatcctctg ttatacttta gagatatttt tgccgtcaaa aaactagaac    1920
acatatatcc tttatttatc ccgatatcga atcgattgta ccacgagtga agggtatagc   1980
tctagttttg gacggtaggg cacctaaagt agacgaaga                            2019
```

<210> SEQ ID NO 4  
<211> LENGTH: 27  
<212> TYPE: DNA  
<213> ORGANISM: artificial sequence  
<220> FEATURE:  
<221> NAME/KEY: misc_feature  
<222> LOCATION: 10  
<223> OTHER INFORMATION: description of artificial sequence: primer. n is any nucleotide.

<400> SEQUENCE: 4
ccttcacytn ttytaycart ayaaycc                                         27

<210> SEQ ID NO 5  
<211> LENGTH: 27  
<212> TYPE: DNA  
<213> ORGANISM: artificial sequence  
<220> FEATURE:  
<223> OTHER INFORMATION: description of artificial sequence: primer

<400> SEQUENCE: 5
cctttcrwar aargtyttdg wwgcgta                                         27

```
<210> SEQ ID NO 6
<211> LENGTH: 760
<212> TYPE: DNA
<213> ORGANISM: Nicotiana tabacum

<400> SEQUENCE: 6
ggtaccccct tcgtagaag gttttggaag cgtagaaatt tccatagtca agtctcaatc       60
ccttccaact atcaaccgaa gtgttatctg gaatatacct gtctttttta atatcgtacg      120
taccaacagt atagtactca aacctagtaa gatccatact attttttaagt acgtacttag    180 aatcttcacc atatttatct aaaccatttg taccttgtaa tgatacaggg aaaaaatcag     240
gacattccca atttcctgta ttagcagttg aatgaagtgg atgtttagcc ttaatccatc     300
tcataaaatc cttacttcta tacattattg ccaatcccct cttttttctc aaacttccca    360
ttataattct ccaatgacca tctttgccca tccaagctgt tgtcgggtca cgaaattggg    420
tcttgttaat gctaatatcc gggacgatta acgggttgtt atcgggcttg atccattcgc    480
gaagatatgg atcggataag ttggccggga cggcgtaatt ttggacttgg gttttattgg    540
catcaactat tccagtgtac aaaataatgg gcttgttacc aggaagaact gttgctgaac    600
cagaccaagt tccatatttg tcaaattgtt tggatggata aattgcaggc tctaaattaa    660
tccaattgat taaatctttt gagactgaat gagcccaaac aatgttgccc catactgatc    720
cttttggatt gtattgataa aacaagtgaa ggggggatcc                          760

<210> SEQ ID NO 7
<211> LENGTH: 29
<212> TYPE: DNA
<213> ORGANISM: artificial sequence
<220> FEATURE:
<223> OTHER INFORMATION: description of artificial sequence: primer

<400> SEQUENCE: 7 atccarttttt kdbkwggttg aaartggwa                                      29

<210> SEQ ID NO 8
<211> LENGTH: 4135
<212> TYPE: DNA
<213> ORGANISM: artificial sequence
<220> FEATURE:
<221> NAME/KEY: unsure
<222> LOCATION: location (1274), (1418), (1585), (1712), (2952), (2953)
<223> OTHER INFORMATION: description of artificial sequence: primer. n
      is any nucleotide

<400> SEQUENCE: 8
tcgagccatt catgttcagc ccattctgga aagttgctac aaccattcct                50
tctgatacat tcggtaaggt catccttact ctgttgaatc gagcgaggaa               100
gtccctcaat ccctctccga gtgattgttt gatggcaaat atatcgttca               150
ctcttgcctc cgcgttttta gccccaacat gggccattat gaacttgtcg               200
gccatctctt cgaatatttc aatggagcgc gcgggcagct gtgaatacca               250
agtcaatgct cctccggtaa gggtctcgcc gaacattttc aacaagatgg               300
aggagacttg ttcttttggag agatcattgc cctttaccgc agtgacataa               350
tgattacatg atcttcgggg tcgtcgtac catcataaat tttcagataa                400
ggtggcatct tgaacgtctt gggtatggca tatggggcgg cttcatcact               450
gtagggttgc tcgactaacc gaccagcgtc tcttttttgga aatatttttg              500 gggcacccgg tattttatcg actctttctt ggtgttctct catttgatcc              550
```

-continued

```
cgaagcattt tattttcgtt ttccatttct tccattttct tcagaatggc        600
cgtgagggtg tcattacctg cattattaat attgtgagtg atacctgtta        650
ctgaaggggg agggtcgtgc tgtttggtca ttgctggtgc aatgcaagtc        700
cttgcatttt ctctaaatac ctcctgagtg ggtttgttga ggatgccggt        750
cagcatattt gtcagccaag cttcgagtag cttcttcacc gctggtggcg        800
cctcttccgt tgtggacgtg aagctcctt taccgcggga tgttgcgata         850
ctgctgtgag ggaggggtga tccacttcgt cggggagagg tgttaggcgt        900
tatgccttcg ccttctattt cggagacctc attgatggtg tttaagaggt        950
tggtagtgag attggccact gccttcatcc tttcttctcc cttacctgcc       1000
atgtcagatc tgggtgtaca aggaagtagg agcttctctt cttcttttt       1050 gtgaattgtg ccagttatag atctaaaaga aactaaagtt ttaactagac       1100
tatcctcaca gacggcgcca aattgtttga ccaaaaaata tagacttttg       1150
attaaattaa ttaatattgt atgacaaagg attaaaccta gttaatgata       1200
ataacttcag atctataatc aattaacagc aatcacggtc atagcagcgt       1250
tgagagaaga ttaaatgtga tgtncattca atatttcaag atcattaatg       1300
ataggggaat atcaagcaat aaataacgat aaatggcatt aaagtaaata       1350
aggagaatga ttcacccaat attgaatgag gtggatgatt cttcttttg       1400 acaatgatga atgatggnca aatactagaa tgttgggacc cttctcggat       1450
ctaatgaaaa aagtatggaa tagtagataa tcgaatctct ttagaaaggt       1500
agtgattgtc ttttatctag agagaaagtc tgcttttcaa agaatatttt       1550
tatcagagaa tattacatcc ccctctctcc ctatntcttt ttctatttat       1600
atgggacatt cctcaatcaa tcctaaaagt acatacacca agaatattca       1650
ataaaatatt tttttgaata ttctattata aaaactagct gttagcactc       1700
gacctcggtc gntattgact actcggttac gagccctgtc atttactaat       1750
cgacctcgat tacatcactt tctacgatac tgcttcatgt caaatcttaa       1800
tgaaagcaga ttttgaccca tacaataata tgacaaaatt gcttccaaag       1850
aaaacatggc tcttatagtg aaatatcgtt agactgttat agaaagatct       1900
gaatttattt ataagaatag tgttttttttc ttttcttttc atatctaagg      1950
agtaaagcaa ccatgaatag aaaaggctta gtaactatat atcaaaggaa       2000
tggtgttttt tctttaaata tggataaaaa tttgtgaata tagaagatta       2050
gatcaattaa caaaggttat ggtggagtgg taagcagagg cggacctatg       2100
tgttatagta agggtcacc cactactaga aatccggtaa agatcgatca        2150 aaaaccgac caacattggt cggtaatggc caaaaactga ccaaaacgcg        2200
atcatttacg tgtgaacggt attttttatgg tcggaaagga ataccgacca      2250
aagttggtcg gaaattaccg accaactttg gtcggtcaat taaattcaaa       2300
aaaaatattg taaaaaaaaa ccgaccaaag ttgatcggta ttttaattat       2350
gtaataaaaa gattcactat ctgggaatcg aaccggggtc tgtactatgg       2400
caagatacta ttctaccact agaccattgg ttcatttttgt tttaagactg      2450 tcttttattt gatttatact cttaattat attttttgcac gaaataaacc       2500 gaccaaagtt ggtcgatttt attaaaaagt aaaattactt accaaagttg       2550
```

```
gtcgattttt ttaaatgatc cgccgaatta accgaccaat tttggtaggt         2600 tttttaata ttaattttta tttattttaa ttgaaaaact aaccaaagtt          2650
agtcggtttc ttgaaacata aatttcgcgg gactcaaaaa tagtttcccg         2700 cattttgcg ccaagaaaaa ccgaccaaag ttggtcggtt tcgtaaaaaa          2750 aaaaaaatt taaaaatat attttaaaaa accgaccaac tttagtcggt           2800
tttttggtcg attttttgac cgaccaaagt tggtcggtcg accttggtcg         2850 gttttttgccg aatttctagt agtgaccgaa ccctgtaagc ttcgggagaa        2900
attttgtata tgtatatgtg tatatcctta aatgattaa tttaaagaac          2950 gnngcaccct gaatactaga agcctttagg ggcactagat gagcagaata         3000
acgtgttctc gtcgcgtaaa aatacttgga tccgcctatg atggtaagta         3050
cttcttcgtc cttaatcaga ggtttcgact tcgagctcca gatataaact         3100
atagactcgt ctttatagca ccttttaata agactatgac ttcatctgat         3150
ttctctataa atactcctca agctttcggt tcttctccat tgttcagttt         3200
ctttctccac atcacagaag tgaaaacaaa acaagaagaa gaagaagaag         3250
aaaaataaag agtttctgtc aaattaagtc caatagggaa aatggagctg         3300
tttggatccc cgttttcatt attggggaga ccatctaatt cataagacca         3350
accccacacg attcttcggt ccttactagg gtcgtagaac gacttagacg         3400
cgtagaaaat gccatagtca agtctcaatc ctttccaacc atcgactgaa         3450
gtgttatctg gaatatacct atcttgtttg gcatcatatg taccaattgt         3500
gtagtactca aacgcggcaa caggaaggct attcttgaga acgtacttaa         3550 cataattttcc gttgtacgat gcatctaaac cattagaacc ttgcaaggaa        3600
acaggaaaaa aatctgggca ttcccaattt cctgttttgg cagatgaatg         3650
aagtggatgc tcagccttga tccatttcat gaaattccta cttctataca         3700
atattgccaa cccaccacgg tttcttgaac ttcctaccac aattctccaa         3750
tgaccatctt tgcccatcca agctgttgtc gggtcacgaa attgggtctt         3800
ggtgatgctg atatccggga cgatcaacgg gttgttatcg ggcttgttcc         3850
attcacggag atatggatcg gataagttgg ccgggacggc gtaattttgg        3900
acttgggtca tgttggcatc taccactcca gtgtacaaaa taatgggctt        3950
gttaccaggg agaatagttg ctgaaccaga ccatgttcca tatttgtcaa        4000
atggtttgga tggataaatt gcaggctcta aattaatcca attgattaag        4050
tcttttgaga ctgaatgagc ccaaacaatg ttgttcattg ttgatccttt        4100
tggattgtac tggtagaata gatgatagac tcgag                       4135
```

<210> SEQ ID NO 9
<211> LENGTH: 19
<212> TYPE: DNA
<213> ORGANISM: artificial sequence
<220> FEATURE:
<223> OTHER INFORMATION: description of artificial sequence: primer

<400> SEQUENCE: 9
cgagttaaca tatgcagct                                          19

```
<210> SEQ ID NO 10
<211> LENGTH: 19
<212> TYPE: DNA
<213> ORGANISM: artificial sequence
<220> FEATURE:
<223> OTHER INFORMATION: description of artificial sequence: primer

<400> SEQUENCE: 10
gcatatgtta actcgagct                                                    19

<210> SEQ ID NO 11
<211> LENGTH: 24
<212> TYPE: DNA
<213> ORGANISM: artificial sequence
<220> FEATURE:
<223> OTHER INFORMATION: description of artificial sequence: primer

<400> SEQUENCE: 11
cttggatccg cctatgatgg taag                                              24

<210> SEQ ID NO 12
<211> LENGTH: 30
<212> TYPE: DNA
<213> ORGANISM: artificial sequence
<220> FEATURE:
<223> OTHER INFORMATION: description of artificial sequence: primer

<400> SEQUENCE: 12
gcgcggatcc tctaaacagc tccattttcc                                        30

<210> SEQ ID NO 13
<211> LENGTH: 30
<212> TYPE: DNA
<213> ORGANISM: artificial sequence
<220> FEATURE:
<223> OTHER INFORMATION: description of artificial sequence: primer

<400> SEQUENCE: 13
ccgtctcgag tctatcatct attctaccag                                        30

<210> SEQ ID NO 14
<211> LENGTH: 24
<212> TYPE: DNA
<213> ORGANISM: artificial sequence
<220> FEATURE:
<223> OTHER INFORMATION: description of artificial sequence: primer

<400> SEQUENCE: 14
gttttcatta ttggggagac catc                                              24

<210> SEQ ID NO 15
<211> LENGTH: 3908
<212> TYPE: DNA
<213> ORGANISM: Nicotiana tabacum
<220> FEATURE:
<223> OTHER INFORMATION: genomic sequence of extracellular invertase
      NIN 88

<400> SEQUENCE: 15
atggagctgt ttagaaaaag ctcttttcat tgtgctttgc cagttttcat                  50
attattggtt tgcttgttta aattttatc taactatgtt gtgtttgctt                  100
tcaattatga cgtttttacg tgcttccaat cctcaaaaga tgctaatatc                 150
acttctaact acagaactgg ttaccatttt caaccccca agaactgtat                  200 gaatggtacg tttctctccc cttccaccca ccccacccc tcttctgttg                  250
```

-continued

| | |
|---|---|
| ttgcttttga tatgtgtata tatatatata tatccatttt ttgctcggta | 300 |
| tcggcattag gatccactaa attcggcatt gagggtaat taggcgtcta | 350 |
| acaaagtcaa ttccataact agggctcgaa cccgagactt ccgattaaaa | 400 |
| atgaaggagt acttaacact tattctgtaa cattaaacaa tagacatcct | 450 |
| actcctctaa actcatttgt atttttaaaa tatctatttt accctcgatc | 500 |
| ttattagcct tcatctactt tttttttttt tactttttta atatcacaat | 550 |
| attttcttat tctatgttat gaatttacct atagtgaaca taaaatttaa | 600 |
| aaaaggtgaa aaacaataat caatcatata cttattgaag ttagaataat | 650 |
| gaaacaaatg ggcgcaatta aaatattaga ataacagatc ttattaatat | 700 |
| caatcaaata aaatttagtt cagtaatata aaaaaataat taaacataga | 750 |
| ggtagatttt ctaagaaatt cctaaaagat tatatattta taacttagaa | 800 |
| aatatttgt taatgaaaat aaatattcaa agatatatac agaacaacaa | 850 |
| caacaacccg accttacccc taccctgggg tagagagact gtttccgata | 900 |
| gaccctcggc tccctccctc caagaactcc ccaccttgcc cttgggatga | 950 |
| ctcgaactca caacctctta gttggaagtg gatggtgctt accactagag | 1000 |
| caacccgctc ttgtccgaag atatatacag aaacatgtaa taagaataa | 1050 |
| aagagaaagt aaaacttaaa tatatagata atattaatgt aacgataaaa | 1100 |
| aagagtaacg ataattgttt ttgcaaattc ataaaggtat tattctagtt | 1150 |
| aaattttatt gagttttaat tatataattt atcataagat attaaaattg | 1200 |
| gtaaaatact taggctaatg ataaaataca tcttatataa tattaaaaaa | 1250 |
| aatagaggag aaattgaaaa tgtcaagggt aaaatagaaa atgcatatga | 1300 |
| taggaggagc gaaatatata ttatttagtg ttggaagagt gatttgattt | 1350 |
| ttaagataaa attaggggat gaaaatgatt tttacacttt aatagataga | 1400 |
| tcctactgaa acacgtgtga gttccaaaag caaaaaacga aaaaggaacc | 1450 |
| agctccctaa taatgagtac ttattataca agtaaataca attagaggac | 1500 |
| actaattgca acccctact tgggaactgt cggcctattg ctttaattac | 1550 |
| ttatactctc actccgttca cttttactta tccaatattc taagtgacat | 1600 |
| ttggacataa gaattgtaaa attccaaaat aggaaaaaaa aatacaagtg | 1650 |
| aaaatgttat ttgaaattta gagttacgtt tggacatgaa tataattttg | 1700 |
| ggttgttttt aaagttttgt gagtgatttg agtgaaaatt ttgaaaaaca | 1750 |
| gttttttgaa gtttttcaaa ttttcgaaaa ttttcaaaat gcatcttcaa | 1800 |
| atgaaaattg aaaattttat gaacaaacgc tgatttcgaa aaaaaagtga | 1850 |
| tttttttgtg gaaaaaagaa aaaaatttct tatgtccaaa cgggctctaa | 1900 |
| aaatagattt tcactttac ttgtcacttt tcgcatatca agagaagaca | 1950 |
| atttcttttt ttctgttata ctcatagtat taattactca tttcaaatca | 2000 |
| ttttttcaaa tccactaaaa atatgtatca attaatatgg gtattatggt | 2050 |
| aaattatgca cttcatttat tatttcttaa ggagtgttca aagtccgtag | 2100 |
| tagacaagta aaagtgaatg gagagagtaa taaattacac ctactttctt | 2150 |
| ggaaatacca gttgagacat acgtagaact tttgctaatt ttttcttatt | 2200 |
| ttttcttaat tatattatat ttgtgtgtga tatgggcaga aggggttggt | 2250 |

| | |
|---|---|
| aagaaggatc ttgtcgcccat cagcaactta caatatttta gggaagacaa | 2300 |
| ataataattt tctgcatttc ctaaattttt gtaatttcac ttttcatttg | 2350 |
| tttattattt gattattcat caatattaaa ttatgcagat ttagtactca | 2400 |
| cattcaattg tttatttaca attttttta attttttct ttatggtctt | 2450 |
| tctcgatgcc ttcaaacata caaatagacc ccaatggtga gtcagaaatt | 2500 |
| ttatcttctt tttatatata taatttaatc accaattatt catttatgat | 2550 |
| actgattttt catgtaatta ccaacagcac caatgtatta caatggagtc | 2600 |
| tatcatctat tctaccagta caatccaaaa ggatcaacaa tgaacaacat | 2650 |
| tgtttgggct cattcagtct caaaagactt aatcaattgg attaatttag | 2700 |
| agcctgcaat ttatccatcc aaaccatttg acaaatatgg aacatggtct | 2750 |
| ggttcagcaa ctattctccc tggtaacaag cccattattt tgtacactgg | 2800 |
| agtggtagat gccaacatga cccaagtcca aaattacgcc gtcccggcca | 2850 |
| acttatccga tccatatctc cgtgaatgga acaagcccga taacaacccg | 2900 |
| ttgatcgtcc cggatatcag catcaccaag acccaatttc gtgacccgac | 2950 |
| aacagcttgg atgggcaaag atggtcattg gagaattgtg gtaggaagtt | 3000 |
| caagaaaccg tggtgggttg gcaatattgt atagaagtag gaatttcatg | 3050 |
| aaatggatca aggctgagca tccacttcat tcatctgcca aaacaggaaa | 3100 |
| ttgggaatgc ccagattttt ttcctgtttc cttgcaaggt tctaatggtt | 3150 |
| tagatgcatc gtacaacgga aaatatgtta agtacgttct caagaatagc | 3200 |
| cttcctgttg ccgcgtttga gtactacaca attggtacat atgatgccaa | 3250 |
| acaagatagg tatattccag ataacacttc agtcgatggt tggaaaggat | 3300 |
| tgagacttga ctatggcatt ttctacgcgt ctaagtcgtt ctacgaccct | 3350 |
| agtaaggacc gaagaatcgt gtggggttgg tcttatgaat tagatggtct | 3400 |
| ccccaataat gaaaacaaca aaggatgggc ctggaattca ggctatcccg | 3450 |
| cgtaaagtat ggcttgattt cagtggtaaa caattagttc aatggcctat | 3500 |
| tgaagaatta aaaactctaa gaaagcaaaa tgtccgattg agcaacaaaa | 3550 |
| ggctggataa tggagaaaag attgaagtta aaggaatcac agcgtcgcag | 3600 |
| gtttagactt ttttctagtt tttaatttgc aagcatttta aataaaattt | 3650 |
| tcttcacaag ttaaggctaa gttgggacat ctattgaaat tgccaggctg | 3700 |
| atgttgaagt gacattctcc ttctctagct tagacaaggc agagccattt | 3750 |
| gatcctagtt gggctgatct ttatgcacaa gatgtttgtg caattaaggg | 3800 |
| ttcaactgtt ccaggtgggc ttgggccatt tggccttgca acattggctt | 3850 |
| ctcaaaactt agaagaatac acacctgttt ttttcagagt gttcaaagct | 3900 |
| cagaattt | 3908 |

<210> SEQ ID NO 16
<211> LENGTH: 24
<212> TYPE: DNA
<213> ORGANISM: artificial sequence
<220> FEATURE:
<223> OTHER INFORMATION: description of artificial sequence: primer -continued

```
<400> SEQUENCE: 16 ctc cat tgt tca gtt tct ttc tcc                                          24

<210> SEQ ID NO 17
<211> LENGTH: 27
<212> TYPE: DNA
<213> ORGANISM: artificial sequence
<220> FEATURE:
<223> OTHER INFORMATION: description of artificial sequence: primer

<400> SEQUENCE: 17 ggt aca tat gat gcc aaa caa gat agg                                      27

<210> SEQ ID NO 18
<211> LENGTH: 27
<212> TYPE: DNA
<213> ORGANISM: artificial sequence
<220> FEATURE:
<223> OTHER INFORMATION: description of artificial sequence: primer

<400> SEQUENCE: 18 gtg gtg gag agc ttt gga gca aaa agg                                      27

<210> SEQ ID NO 19
<211> LENGTH: 24
<212> TYPE: DNA
<213> ORGANISM: artificial sequence
<220> FEATURE:
<223> OTHER INFORMATION: description of artificial sequence: primer

<400> SEQUENCE: 19 gtt gca ctt cgt ttg tcc gaa agc                                          24

<210> SEQ ID NO 20
<211> LENGTH: 24
<212> TYPE: DNA
<213> ORGANISM: artificial sequence
<220> FEATURE:
<223> OTHER INFORMATION: description of artificial sequence: primer

<400> SEQUENCE: 20 gga gtt tga ttg ata act cag tag                                          24
```

ANTIBODY KIT FOR THE DETECTION OF TADG-15 PROTEIN

CROSS-REFERENCE TO RELATED APPLICATION

This application in a continuation-in-part of U.S. Ser. No. 09/027,337, filed Feb. 20, 1998 Now U.S. Pat. No. 5,972, 616 and thereby claims the benefit of priority under 35 USC §120.

BACKGROUND OF THE INVENTION

1. Field of the Invention

The present invention relates generally to the fields of cellular biology and the diagnosis of neoplastic disease. More specifically, the present invention relates to an extracellular serine protease, termed tumor antigen-derived gene 15 (TADG-15), which is overexpressed in carcinomas.

2. Description of the Related Art

Extracellular proteases have been directly associated with tumor growth, shedding of tumor cells and invasion of target organs. Individual classes of proteases are involved in, but not limited to, (a) digestion of stroma surrounding the initial tumor area, (b) digestion of the cellular adhesion molecules to allow dissociation of tumor cells; and (c) invasion of the basement membrane for metastatic growth and activation of both tumor growth factors and angiogenic factors.

In the process of cancer progression and invasion, proteases mediate specific proteolysis and contribute to the removal of extracellular matrix components surrounding tumor cells, the digestion of intercellular adhesion molecules to allow dissociation of malignant cells and the activation of many growth and angiogenic factors.[1-3] Depending on the nature of their catalytic domain, proteases are classified into four families: serine proteases, metalloproteases, aspartic proteases and cysteine proteases.[3] Among these proteases, the metalloproteases have been well studied in relation to tumor growth and progression, and they are known to be capable of degrading the extracellular matrix, thereby enhancing the invasive potential of malignant cells.[1,4,5] For serine proteases, previous studies have demonstrated an increased production of plasminogen activator in tumor cells and a positive correlation between plasminogen activator activity and aggressiveness of cancer. Prostate specific antigen (a serine protease) has also been widely used as an indicator of abnormal prostate growth.[8] More recently, several other serine proteases have been reported, viz. hepsin and the stratum corneum chymotryptic enzyme (SCCE), which are overexpressed in ovarian cancer and which may contribute to malignant progression by increasing the extracellular lytic activity of these tumor cells.[9]

The prior art is deficient in the lack of effective means of screening to identify proteases overexpressed in carcinoma. The present invention fulfills this longstanding need and desire in the art.

SUMMARY OF THE INVENTION

The present invention discloses a screening program to identify proteases overexpressed in carcinoma by examining PCR products amplified using differential display in early stage tumors and metastatic tumors compared to that of normal tissues. The approach herein to identify candidate genes overexpressed in tumor cells has been to utilize the well conserved domains surrounding the triad of amino acids (His-Asp-Ser) prototypical of the catalytic domain of serine proteases. Herein, evidence is presented for a unique form of serine protease not previously described in the literature which is highly expressed in ovarian carcinomas. Through the screening approach using differential PCR amplification of normal, low malignant potential and overt carcinomas, a PCR product present only in carcinoma was subcloned and sequenced, and was found to have a catalytic domain which was consistent with the serine protease family. Reported herein is the complete cloning and sequencing of this transcript and evidence for its expression in ovarian tumor cells.

In one embodiment of the present invention, there is provided a DNA encoding a tumor antigen-derived gene (TADG-15) protein, selected from the following: (a) an isolated DNA which encodes a TADG-15 protein; (b) an isolated DNA which hybridizes under high stringency conditions to the isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein. The embodiment further includes a vector comprising the TADG-15 DNA and regulatory elements necessary for expression of the DNA in a cell. Additionally embodied is a vector in which the TADG-15 DNA is positioned in reverse orientation relative to the regulatory elements such that TADG-15 antisense mRNA is produced.

In another embodiment of the present invention, there is provided an isolated and purified TADG-15 protein coded for by DNA selected from the following: (a) an isolated DNA which encodes a TADG-15 protein; (b) an isolated DNA which hybridizes under high stringency conditions to isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein.

In yet another embodiment of the present invention, there is provided a method for detecting TADG-15 mRNA in a sample, comprising the steps of: (a) contacting a sample with a probe which is specific for TADG-15; and (b) detecting binding of the probe to TADG-15 mRNA in the sample. In still yet another embodiment of the present invention, there is provided a kit for detecting TADG-15 mRNA, comprising: an oligonucleotide probe specific for TADG-15. A label for detection is further embodied in the kit.

The present invention additionally embodies a method of detecting TADG-15 protein in a sample, comprising the steps of: (a) contacting a sample with an antibody which is specific for TADG-15 or a fragment thereof; and (b) detecting binding of the antibody to TADG-15 protein in the sample. Similarly, the present invention also embodies a kit for detecting TADG-15 protein, comprising: an antibody specific for TADG-15 protein or a fragment thereof. Means for detection of the antibody is further embodied in the kit.

In another embodiment, the present invention provides an antibody specific for the TADG-15 protein or a fragment thereof.

In yet another embodiment, the present invention provides a method of screening for compounds that inhibit TADG-15, comprising the steps of: (a) contacting a sample comprising TADG-15 protein with a compound; and (b) assaying for TADG-15 protease activity. Typically, a decrease in the TADG-15 protease activity in the presence of the compound relative to TADG-15 protease activity in the absence of the compound is indicative of a compound that inhibits TADG-15.

In still yet another embodiment of the present invention, there is provided a method of inhibiting expression of TADG-15 in a cell, comprising the step of: (a) introducing a vector into a cell, whereupon expression of the vector produces TADG-15 antisense mRNA in the cell which hybridizes to endogenous TADG-15 mRNA, thereby inhibiting expression of TADG-15 in the cell.

Further embodied by the present invention, there is provided a method of inhibiting a TADG-15 protein in a cell, comprising the step of: (a) introducing an antibody specific for a TADG-15 protein or a fragment thereof into a cell, whereupon binding of the antibody to the TADG-15 protein inhibits the TADG-15 protein.

In an embodiment of the present invention, there is provided a method of targeted therapy to an individual, comprising the step of: (a) administering a compound containing a targeting moiety and a therapeutic moiety to an individual, wherein the targeting moiety is specific for TADG-15.

In an embodiment of the present invention, there is provided a method of diagnosing cancer in an individual, comprising the steps of: (a) obtaining a biological sample from an individual; and (b) detecting TADG-15 in the sample, wherein the presence of TADG-15 in the sample is indicative of the presence of carcinoma in the individual and the absence of TADG-15 in the sample is indicative of the absence of carcinoma in the individual.

In another embodiment of the present invention, there is provided a method of vaccinating an individual against TADG-15, comprising the steps of: (a) inoculating an individual with a TADG-15 protein or fragment thereof that lacks TADG-15 protease activity, wherein the inoculation with the TADG-15 protein or fragment thereof elicits an immune response in the individual, thereby vaccinating the individual against TADG-15.

In an embodiment of the present invention, there is provided a method of producing immune-activated cells directed toward TADG-15, comprising the steps of: exposing dendritic cells to a TADG-15 protein or fragment thereof that lacks TADG-15 protease activity, wherein the exposure to said TADG-15 protein or fragment thereof activates the dendritic cells, thereby producing immune-activated cells directed toward TADG-15.

In another embodiment of the present invention, there is provided an immunogenic composition, comprising an immunogenic fragment of a TADG-15 protein and an appropriate adjuvant.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A and 1B show a comparison of the serine protease catalytic domain of TADG-15 with Hepsin (Heps, SEQ ID No. 3), SCCE (SEQ ID No. 4), Trypsin, (Try, SEQ ID No. 5), Chymotrypsin (Chymb, SEQ ID No. 6), Factor 7 (Fac7, SEQ ID No. 7) and Tissue plasmiogen activator (Tpa, SEQ ID No. 8). The asterisks indicate conserved amino acids of catalytic triad.

FIGS. 2A–2D show the nucleotide sequence of the TADG-15 cDNA and the derived amino acid sequence of the TADG-15 protein. The putative start codon is located at nucleotides 23–25. The potential transmembrane sequence is underlined. Possible N-linked glycosylation sites are indicated by a broken line. The asterisks indicate conserved cysteine residues of CUB domain. The SDE-motifs of the LDL receptor ligand binding repeat-like domain are boxed. The arrow shows the arginine-valine bond cleaved upon activation. The conserved amino acids of the catalytic triad; histidine, aspartic acid and serine residues are circled.

FIG. 3 shows the amino acid sequence of the TADG-15 protease, including functional sites and domains.

Figure 10A:
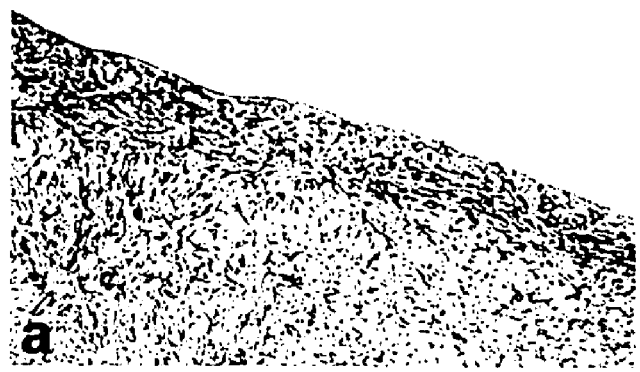
FIG. 10 shows that immunohistochemical staining of normal ovarian epithelium (FIG. 10A) with a polyclonal antibody to a TADG-15 protease peptide shows no staining of the stroma or epithelium. However, antibody staining of carcinomas confirms the presence of TADG-15 expression in the cytoplasm of a serous low malignant potential tumor (FIG. 10B); a mucinous low malignant potential tumor (FIG.
Figure 10B:
Figure 10C:
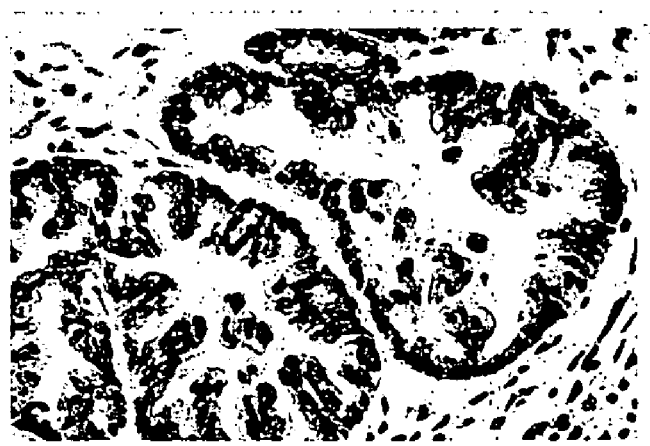
Figure 10D:
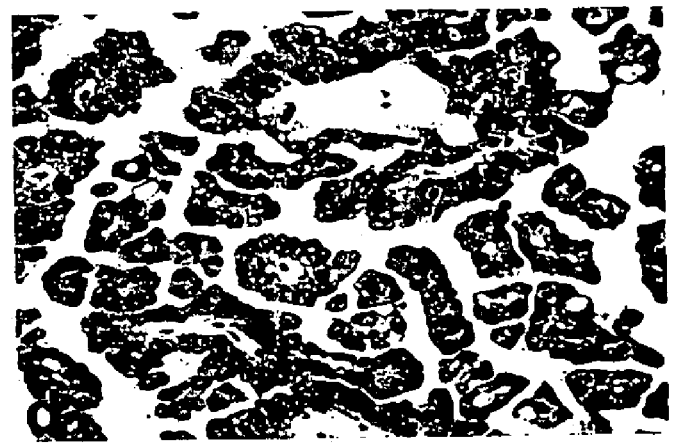
Figure 10E:

10C); a serous carcinoma (FIG. 10D); and its presence in both the cytoplasm and cell surface of an endometrioid carcinoma (FIG. 10E).

FIGS. 11A and 11B show and alignment of the human TADG15 protein sequence with that of mouse epithin which demonstrates that the proteins are 84% similar and 81% identical over 843 amino acids. Residues that are identical between the two proteins are indicated by a "-" while he "*" symbol represents the TADG15 translation termination. The most significant difference between these .two proteins lies in the carboxy-termini, which for epithin, includes 47 amino acids that are not present in TADG15.

Figure 12B:
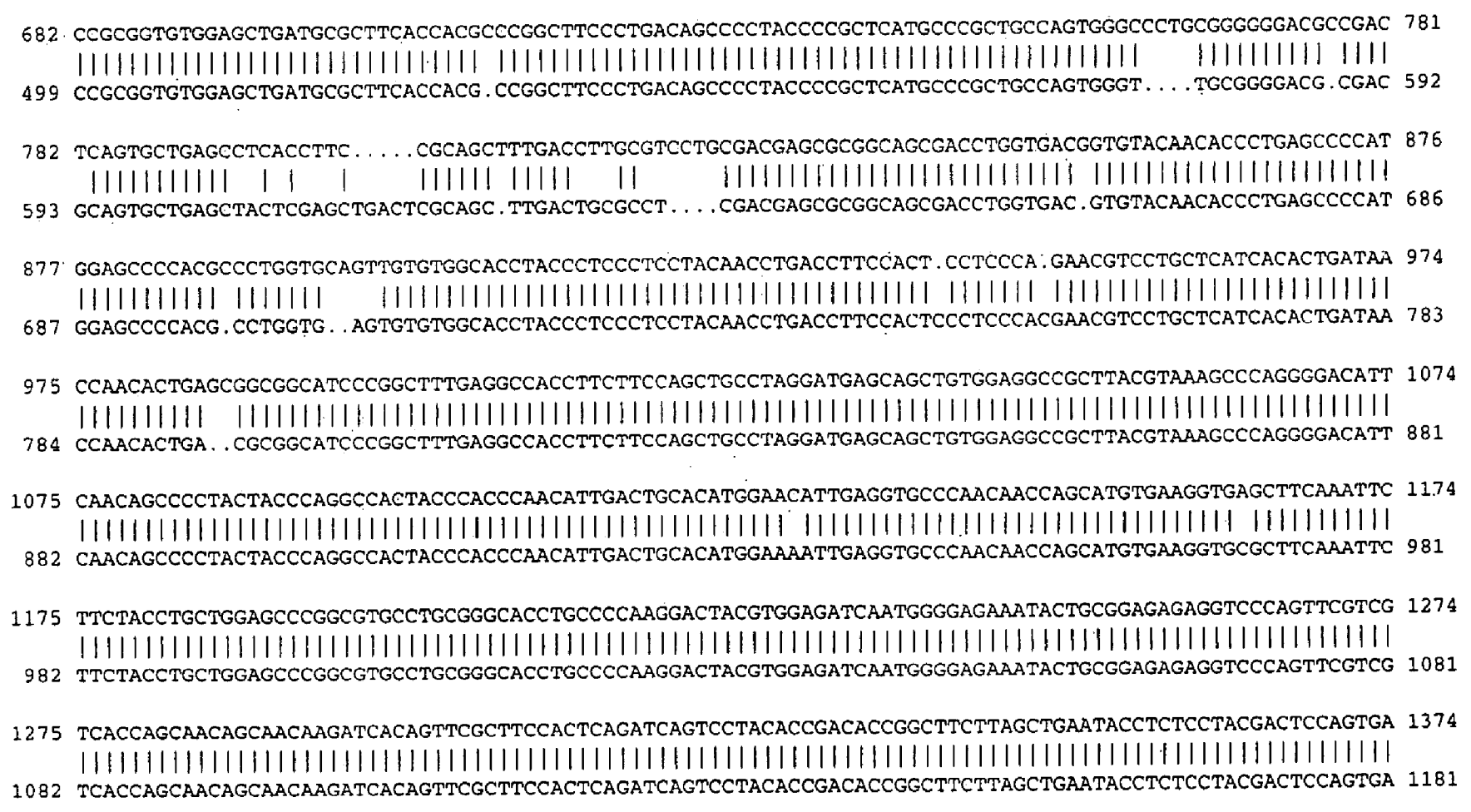
Figure 12D:
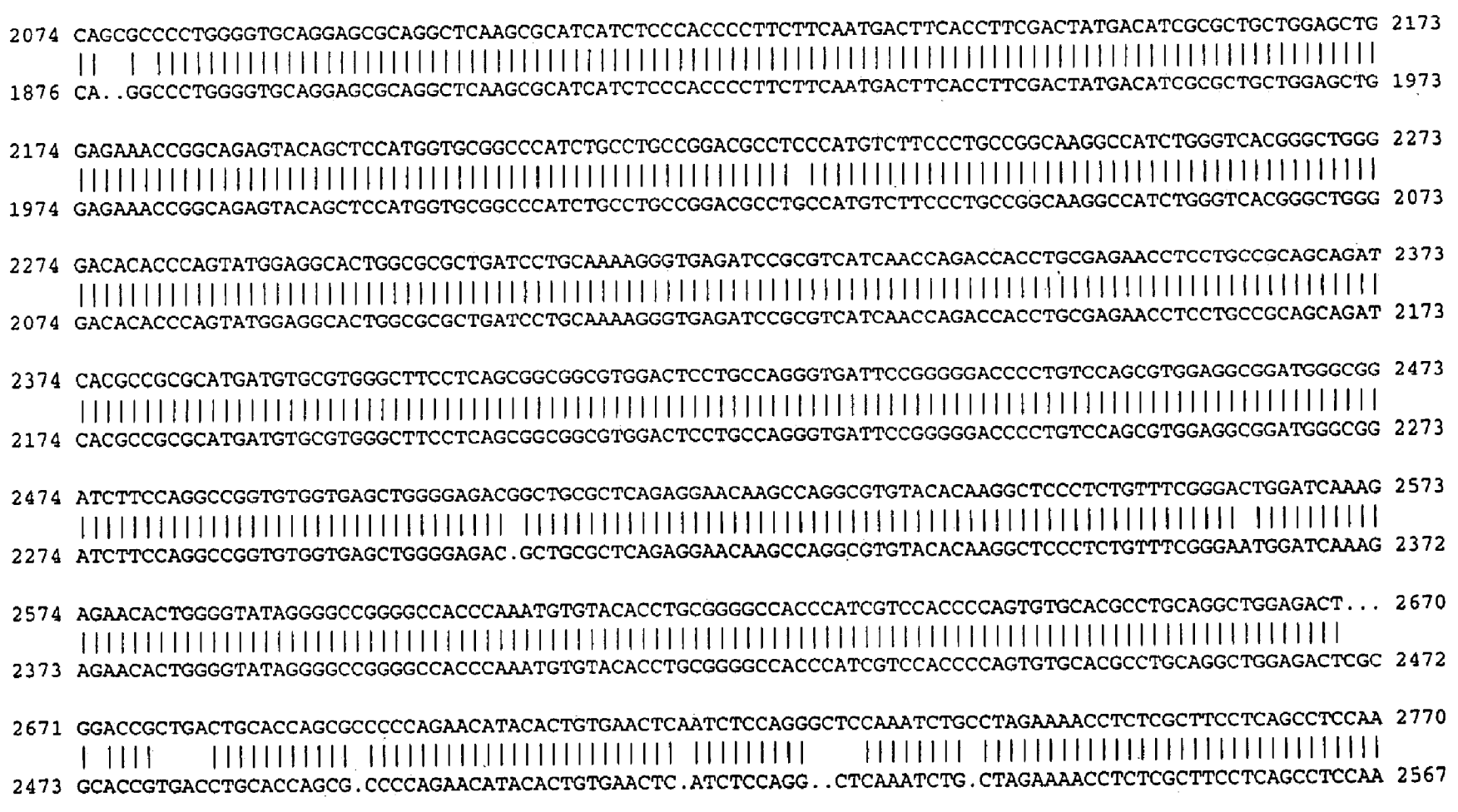

FIGS. 12A–12E show a nucleotide sequence comparison between TADG-15 and human SNC-19 (GeneBank Accession No. #U20428.

DETAILED DESCRIPTION OF THE INVENTION

Proteases have been implicated in the extracellular modulation required for tumor growth and invasion. In an effort to categorize those proteases contributing to ovarian carcinoma progression, redundant primers directed towards conserved amino acid domains surrounding the catalytic triad of His, Asp and Ser were utilized to amplify serine proteases differentially expressed in carcinomas. Using this method, a serine protease named TADG-15 (tumor antigen-derived gene 15) has been identified that is overexpressed in ovarian tumors. TADG-15 appears to be a transmembrane multidomain serine protease. TADG-15 is highly overexpressed in ovarian tumors based on PCR, Northern blot and immunolocalization.

The TADG-15 cDNA is 3147 base pairs long (SEQ ID No. 1.) encoding for a 855 amino acid protein (SEQ ID No. 2). The availability of the TADG-15 gene provides numerous utilities. For example, the TADG-15 gene can be used as a diagnostic or therapeutic target in ovarian and other carcinomas, including breast, prostate, lung and colon.

The present invention is directed to DNA encoding a tumor antigen-derived gene (TADG-15) protein, selected from the following: (a) an isolated DNA which encodes a TADG-15 protein; (b) an isolated DNA which hybridizes under high stringency conditions to the isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein. It is preferred that the DNA has the sequence shown in SEQ ID No. 1 and the TADG-15 protein has the amino acid sequence shown in SEQ ID No. 2.

The present invention is directed toward a vector comprising the TADG-15 DNA and regulatory elements necessary for expression of the DNA in a cell, or a vector in which the TADG-15 DNA is positioned in reverse orientation relative to the regulatory elements such that TADG-15 antisense mRNA is produced. Generally, the DNA encodes a TADG-15 protein having the amino acid sequence shown in SEQ ID No. 2. The invention is also directed toward host cells transfected with either of the above-described vector (s). Representative host cells are bacterial cells, mammalian cells, plant cells and insect cells. Preferably, the bacterial cell is E. coli.

The present invention is directed toward an isolated and purified TADG-15 protein coded for by DNA selected from the following: (a) an isolated DNA which encodes a TADG-15 protein; (b) an isolated DNA which hybridizes under high stringency conditions to isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein. Preferably, the protein has the amino acid sequence shown in SEQ ID No. 2.

The present invention is directed toward a method for detecting TADG-15 mRNA in a sample, comprising the steps of: (a) contacting a sample with a probe which is specific for TADG-15; and (b) detecting binding of the probe to TADG-15 mRNA in the sample. The present invention is also directed toward a method of detecting TADG-15 protein in a sample, comprising the steps of: (a) contacting a sample with an antibody which is specific for TADG-15 or a fragment thereof; and (b) detecting binding of the antibody to TADG-15 protein in the sample. Generally, the sample is a biological sample; preferably, the biological sample is from an individual; and typically, the individual is suspected of having cancer.

The present invention is directed toward a kit for detecting TADG-15 mRNA, comprising: an oligonucleotide probe, wherein the probe is specific for TADG-15. The kit may further comprise: a label with which to label the probe; and means for detecting the label. The present invention is additionally directed to a kit for detecting TADG-15 protein, comprising: an antibody which is specific for TADG-15 protein or a fragment thereof. The kit may further comprise: means to detect the antibody.

The present invention is directed toward a antibody which is specific for TADG-15 protein or a fragment thereof.

The present invention is directed toward a method of screening for compounds that inhibit TADG-15, comprising the steps of: (a) contacting a sample containing TADG-15 protein with a compound; and (b) assaying for TADG-15 protease activity. Typically, a decrease in the TADG-15 protease activity in the presence of the compound relative to TADG-15 protease activity in the absence of the compound is indicative of a compound that inhibits TADG-15.

The present invention is directed toward a method of inhibiting expression of TADG-15 in a cell, comprising the step of: (a) introducing a vector expressing TADG-15 antisense mRNA into a cell, which hybridizes to endogenous TADG-15 mRNA, thereby inhibiting expression of TADG-15 in the cell. Generally, the inhibition of TADG-15 expression is for treating cancer.

The present invention is directed toward a method of inhibiting a TADG-15 protein in a cell, comprising the step of: (a) introducing an antibody specific for a TADG-15 protein or a fragment thereof into a cell, which inhibits the TADG-15 protein. Generally, the inhibition of the TADG-15 protein is for treating cancer.

The present invention is directed toward a method of targeted therapy to an individual, comprising the step of: (a) administering a compound having a targeting moiety and a therapeutic moiety to an individual, wherein the targeting moiety is specific for TADG-15. Representative targeting moiety are an antibody specific for TADG-15 and a ligand or ligand binding domain, (e.g., CUB, LDLR, protease and extracellular) that binds TADG-15. Likewise, a representative therapeutic moiety is a radioisotope, a toxin, a chemotherapeutic agent and immune stimulants. Typically, the above-described method is useful when the individual suffers from ovarian cancer, breast cancer or cancers of the prostate, lung, colon and cervix.

The present invention is directed toward a method of diagnosing cancer in an individual, comprising the steps of: (a) obtaining a biological sample from an individual; and (b)

detecting TADG-15 in the sample. Generally, the presence of TADG-15 in the sample is indicative of the presence of carcinoma in the individual, and the absence of TADG-15 in the sample is indicative of the absence of carcinoma in the individual. Generally, the biological sample is blood, ascites fluid, urine, tears, saliva or interstitial fluid. Typical means of detecting TADG-15 are by Northern blot, Western blot, PCR, dot blot, ELIZA, radioimmunoassay, DNA chips or tumor cell labeling. This method may be useful in diagnosing cancers such as ovarian, breast and other cancers in which TADG-15 is overexpressed, such as lung, prostate and colon cancers.

The present invention is also directed to an antisense oligonucleotide having the nucleotide sequence complementary to a TADG-15 mRNA sequence. The present invention is also directed to a composition comprising such an antisense oligonucleotide according and a physiologically acceptable carrier therefore.

The present invention is also directed to a method of treating a neoplastic state in an individual syndrome in an individual in need of such treatment, comprising the step of administering to said individual an effective dose of an antisense oligonucleotide of. Preferably, the neoplastic state is selected from the group consisting of from ovarian cancer, breast cancer, lung cancer, prostate cancer, colon cancer and other cancers in which TADG-15 is overexpressed. For such therapy, the oligonucleotides alone or in combination with other anti-neoplastic agents can be formulated for a variety of modes of administration, including systemic, topical or localized administration. Techniques and formulations generally can be found in *Remington's Pharmaceutical Sciences*, Mack Publishing Co., Easton, Pa. The oligonucleotide active ingredient is generally combined with a pharamceutically accceptable carrier such as a diluent or excipient which can include fillers, extenders, binders, wetting agents, disintergrants, surface active agents or lubricants, depending on the nature of the mode of administration and dosage forms. Typical dosage forms include tablets, powders, liquid preparations including suspensions, emulsions, and solutions, granules, capsules and suppositories, as well as liquid preparations for injections, including liposome preparations.

For systemic administration, injection is preferred, including intramuscular, intravenous, intraperitoneal and subcutaneous. For injection, the oligonucleotides of the invention are formulated in liquid solutions, preferably in physiologically compatible buffers. In addition, the oligonucleotides can be formulated in solid form and redissolved or suspended immediately prior to use. Lyophilized forms are also inclded. Dosages that can be used for systemic administration preferably range from about 0.01 mg/kg to 50 mg/kg administered once or twice per day. However, different dosing schedules can be utilized depending on (1) the potency of an individual oligonucleotide at inhibiting the activity of its target DNA, (2) the severity or extent of the pathological disease state, or (3) the pharmacokinetic behavior of a given oligonucleotide.

The present invention is directed toward a method of vaccinating an individual against TADG-15 overexpression, comprising the steps of: (a) inoculating an individual with a TADG-15 protein or fragment thereof which lacks TADG-15 protease activity. The inoculation with the TADG-15 protein or fragment thereof elicits an immune response in the individual, thereby vaccinating the individual against TADG-15. The vaccination with TADG-15 described herein is intended for an individual who has cancer, is suspected of having cancer or is at risk of getting cancer. Generally, the TADG-15 fragment useful for vaccinating an individual are 9-residue fragments up to 20-residue fragments, with preferred 9-residue fragments shown in SEQ ID Nos. 2, 19, 20, 21, 29, 39, 49, 50, 59, 79, 80, 81, 82, 83, 84, 89 and 90.

The present invention is directed toward a method of producing immune-activated cells directed toward TADG-15, comprising the steps of: exposing dendritic cells to a TADG-15 protein or fragment thereof that lacks TADG-15 protease activity, wherein exposure to the TADG-15 protein or fragment thereof activates the dendritic cells, thereby producing immune-activated cells directed toward TADG-15. Representative immune-activated cells are B-cells, T-cells and dendrites. Generally, the TADG-15 fragment is a 9-residue fragment up to a 20-residue fragment, with preferable 9-residue fragments shown in SEQ ID Nos. 2, 19, 20, 21, 29, 39, 49, 50, 59, 79, 80, 81, 82, 83, 84, 89 and 90. Preferably, the dendritic cells are isolated from an individual prior to exposure, and the activated dendritic cells reintroduced into the individual subsequent to exposure. Typically, the individual for which this method may apply has cancer, is suspected of having cancer or is at risk of getting cancer.

The present invention is directed toward an immunogenic composition, comprising an immunogenic fragment of a TADG-15 protein and an appropriate adjuvant. Generally, the fragment is a 9-residue fragment up to a 20-residue fragment, with preferred 9-residue fragments shown in SEQ ID Nos. 2, 19, 20, 21, 29, 39, 49, 50, 59, 79, 80, 81, 82, 83, 84, 89 and 90.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984). Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are used as in customary in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. A "vector" may further be defined as a replicable nucleic acid construct, e.g., a plasmid or viral nucleic acid.

A "DNA molecule" refers to the polymeric form of deoxyribonucleotides (adenine, guanine, thymine, or cytosine) in its either single-stranded form or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. The structure is discussed herein according to the normal convention of giving only the sequence in the 5' to 3' direction along the nontranscribed strand of DNA (i.e., the strand having a sequence homologous to the mRNA).

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See, for example, techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses. In general, expression vectors contain promoter sequences which facilitate the efficient transcription of the inserted DNA fragment and are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters typically contain Shine-Dalgarno ribosome-binding sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences, having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-15 protein of the present invention can be used to transform a host using any of the techniques commonly known to those of ordinary skill in the art. Especially preferred is the use of a vector containing coding sequences for the gene which encodes a human TADG-15 protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

Figure 4:
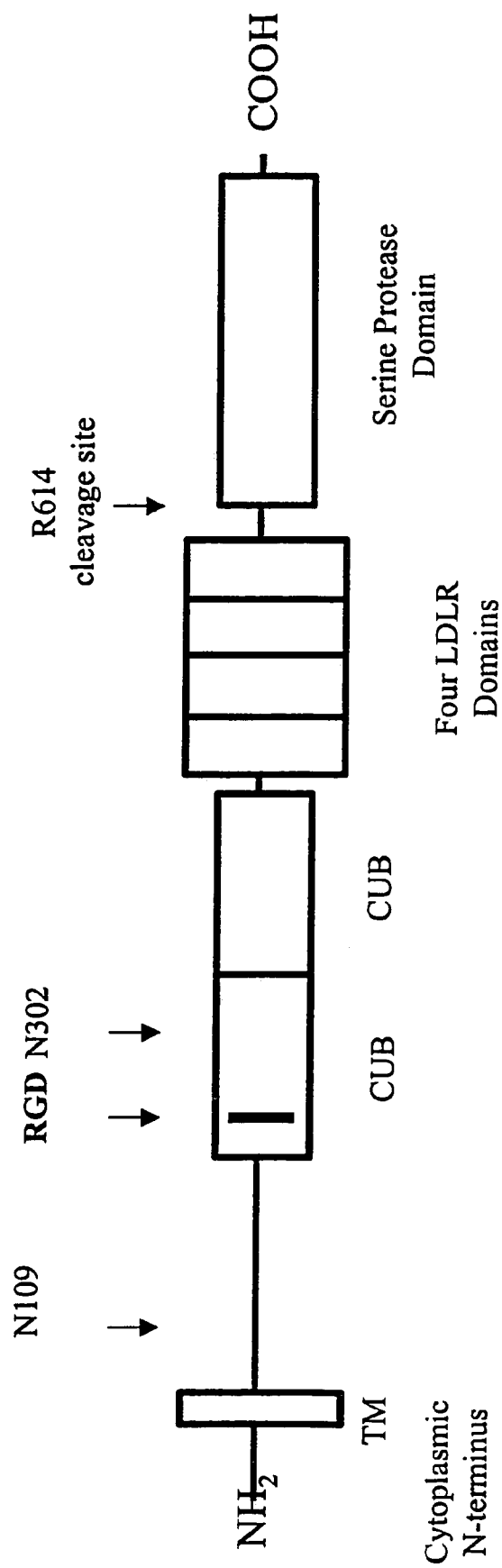
FIG. 4 shows a diagram of the TADG-15 protein. 1; cytoplasmic domain, (aa #1–54), 2; transmembrane domain (aa #55–57), 3; extracellular domain (aa #78–213), 4–5; CUB repeat (aa #214–447), 6–9; LDL receptor ligand binding repeat (class A motif) like domain (aa #453–602), 10; serine protease (aa #615–855).

The invention includes a substantially pure DNA encoding a TADG-15 protein, a DNA strand which will hybridize at high stringency to a probe containing a sequence of at least 15 consecutive nucleotides of (SEQ ID No. 1). The protein encoded by the DNA of this invention may share at least 80% sequence identity (preferably 85%, more preferably 90%, and most preferably 95%) with the amino acids listed in FIGS. 3 and 4 (SEQ ID No. 2). More preferably, the DNA includes the coding sequence of the nucleotides of FIGS. 2A–2D (SEQ ID No. 1), or a degenerate variant of such a sequence. This invention also includes a substantially pure DNA containing a sequence of at least 15 consecutive nucleotides (preferably 20, more preferably 30, even more preferably 50, and most preferably all) of the region from nucleotides 1 to 3147 of the nucleotides shown in FIGS. 2A–2D (SEQ ID No. 1).

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in FIGS. 2A–2D (SEQ ID No. 1) and which encodes an alternative splice variant of TADG-15.

By a "substantially pure protein" is meant a protein which has been separated from at least some of those components which naturally accompany it. Typically, the protein is substantially pure when it is at least 60% (by weight) free from the proteins and other naturally-occurring organic molecules with which it is naturally associated in vivo. Preferably, the purity of the preparation (by weight) is at least 75%, more preferably at feast 90%, and most preferably at least 99%. A substantially pure TADG-15 protein may be obtained, for example, by extraction from a natural source; by expression of a recombinant nucleic acid encoding a TADG-15 polypeptide; or by chemically synthesizing the protein. Purity can be measured by any appropriate method, e.g., column chromatography, such as immunoaffinity chromatography using an antibody specific for TADG-15, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in E. coli, other prokaryotes, or any other organism in which they do not naturally occur.

The term "oligonucleotide", as used herein, is defined as a molecule comprised of two or more ribonucleotides, preferably more than three. Its exact size will depend upon many factors, which, in turn, depend upon the ultimate function and use of the oligonucleotide. The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 15–25 or more nucleotides, depending upon the complexity of the target sequence, although it may contain fewer nucleotides.

The primers herein are selected to be "substantially" complementary to particular target DNA sequences. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and form the template for synthesis of the extension product.

The probe to which the DNA of the invention hybridizes preferably consists of a sequence of at least 20 consecutive nucleotides, more preferably 40 nucleotides, even more preferably 50 nucleotides, and most preferably 100-nucleotides or more (up to –100%) of the coding sequence of the nucleotides listed in FIGS. 2A–2D (SEQ ID No. 1) or the complement thereof. Such a probe is useful for detecting expression of TADG-15 in a cell by a method including the steps of (a) contacting mRNA obtained from the cell with a labeled TADG-15 hybridization probe; and (b) detecting hybridization of the probe with the mRNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

The DNA may have at least about 70% sequence identity to the coding sequence of the nucleotides listed in FIGS. 2A–2D (SEQ ID No. 1), preferably at least 75% (e.g., at least 80%); and most preferably at least 90%. The identity between two sequences is a direct function of the number of matching or identical positions. When a position in both of the two sequences is occupied by same monomeric subunit e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group (GCG), University of Wisconsin Biotechnology Center, 1710 University Avenue, Madison, Wis. 53705).

The present invention comprises a vector comprising a DNA sequence which encodes a human TADG-15 protein, wherein said vector is capable of replication in a host, and comprises, in operable linkage: a) an origin of replication; b) a promoter; and c) a DNA sequence coding for said TADG-15 protein. Preferably, the vector of the present invention contains a portion of the DNA sequence shown in SEQ ID No. 1. Vectors may be used to amplify and/or express nucleic acid encoding a TADG-15 protein or fragment thereof.

In addition to substantially full-length proteins, the invention also includes fragments (e.g., antigenic fragments) of the TADG-15 protein (SEQ ID No. 2). As used herein, "fragment," as applied to a polypeptide, will ordinarily be at least 6 residues, more typically at least 9–12 residues, and preferably at least 13–20 residues in length, but less than the entire, intact sequence. Alternatively, a fragment may be an individual domain of 20–120 residues from SEQ ID No. 2. Fragments of the TADG-15 protein can be generated by methods known to those skilled in the art, e.g., by enzymatic digestion of naturally occurring or recombinant TADG-15 protein, by recombinant DNA techniques using an expression vector that encodes a defined fragment of TADG-15, or by chemical synthesis. The ability of a candidate fragment to exhibit a characteristic of TADG-15 (e.g., binding to an antibody specific for TADG-15) can be assessed by methods described herein. Purified TADG-15 or antigenic fragments of TADG-15 can be used to generate new antibodies or to test existing antibodies (e.g., as positive controls in a diagnostic assay) by employing standard protocols known to those skilled in the art. Included in this invention is polyclonal antisera generated by using TADG-15 or a fragment of TADG-15 as the immunogen in, e.g., rabbits. Standard protocols for monoclonal and polyclonal antibody production known to those skilled in this art are employed. The monoclonal antibodies generated by this procedure can be screened for the ability to identify recombinant TADG-15 cDNA clones, and to distinguish them from other cDNA clones.

Further included in this invention are TADG-15 proteins which are encoded, at least in part, by portions of SEQ ID No. 2, e.g., products of alternative mRNA splicing or alternative protein processing events, or in which a section of TADG-15 sequence has been deleted. The fragment, or the intact TADG-15 polypeptide, may be covalently linked to another polypeptide, e.g., one which acts as a label, a ligand or a means to increase antigenicity.

The invention also includes a polyclonal or monoclonal antibody which specifically binds to TADG-15. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity, of one antibody, e.g., of murine origin, and the remaining portions of another antibody, e.g., of human origin.

In one embodiment, the antibody, or a fragment thereof, may be linked to a toxin or to a detectable label, e.g., a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known and used by those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting TADG-15 protein in a biological sample, which includes the steps of contacting the sample with the labeled antibody, e.g., radioactively tagged antibody specific for TADG-15, and determining whether the antibody binds to a component of the sample. Antibodies to the TADG-15 protein can be used in an immunoassay to detect increased levels of TADG-15 protein expression in tissues suspected of neoplastic transformation. These same uses can be achieved with Northern blot assays and analyses.

As described herein, the invention provides a number of diagnostic advantages and uses. For example, the TADG-15 protein is useful in diagnosing cancer in different tissues since this protein is highly overexpressed in tumor cells. Antibodies (or antigen-binding fragments thereof) which bind to an epitope specific for TADG-15, are useful in a method of detecting TADG-15 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for TADG-15, and detecting the TADG-15 protein using standard immunoassay techniques such as an ELISA. Antibody binding to the biological sample indicates that the sample contains a component which specifically binds to an epitope within TADG-15.

Likewise, a standard Northern blot assay can be used to ascertain the relative amounts of TADG-15 mRNA in a cell or tissue obtained from a patient suspected of having cancer, in accordance with conventional Northern hybridization techniques known to those of ordinary skill in the art. This Northern assay uses a hybridization probe, e.g., radiolabelled TADG-15 cDNA, either containing the full-length, single stranded DNA having a sequence complementary to SEQ ID. No. 1 (FIGS. 2A–2D), or a fragment of that DNA sequence at least 20 (preferably at least 30, more preferably at least 50, and most preferably at least 100 consecutive nucleotides in length). The DNA hybridization probe can be labeled by any of the many different methods know to those skilled in this art.

The following examples are given for the purpose of illustrating various embodiments of the invention and are not meant to limit the present invention in any fashion.

EXAMPLE 1

Tissue Collection and Storage

Upon patient hysterectomy, bilateral salpingo-oophorectomy, or surgical removal of neoplastic tissue, the specimen is retrieved and placed on ice. The specimen was then taken to the resident pathologist for isolation and identification of specific tissue samples. Finally, the sample was frozen in liquid nitrogen, logged into the laboratory record and stored at –80° C.

Additional specimens were frequently obtained from the Cooperative Human Tissue Network (CHTN). These samples were prepared by the CHTN and shipped on dry ice. Upon arrival, these specimens (e.g., blood (serum), urine, saliva, tears and insterstitial fluid) were logged into the laboratory record and stored at –80° C. Participation of the following divisions of the Cooperative Human Tissue Network (CHTN) in providing tumor tissues is acknowledged: Western Division, Case Western Reserve University, (Cleveland, Ohio); Midwestern Division, Ohio state University, (Columbus, Ohio); Eastern Division, NDRI, (Philadelphia, Pa.); Pediatric Division, Children's. Hospital, (Columbus, Ohio); Southern Division, University of Alabama at Birmingham, (Birmingham, Ala.).

EXAMPLE 2 mRNA Isolation and cDNA Synthesis

Forty-one ovarian tumors (10 low malignant potential tumors and 31 carcinomas) and 10 normal ovaries were obtained from surgical specimens and frozen in liquid nitrogen. The human ovarian carcinoma cell lines SW626 and CAOV3, and the human breast carcinoma cell lines MDA-MB-231 and MDA-MB-435S, were purchased from the American Type Culture Collection (Rockville, Md.). Cells were cultured to sub-confluency in Dulbecco's modified Eagle's medium supplemented with 10% (v/v) fetal bovine serum and antibiotics.

Messenger RNA (mRNA) isolation was performed according to the manufacturer's instructions using the Mini RiboSep™ Ultra mRNA Isolation Kit purchased from Becton Dickinson. In this procedure, polyA$^+$ mRNA was isolated directly from the tissue lysate using the affinity chromatography media oligo(dT) cellulose. The amount of mRNA recovered was quantitated by UV spectrophotometry.

First-strand complementary DNA (cDNA) was synthesized using 5.0 μg of mRNA and either random hexamer or oligo(dT) primers according to the manufacturer's protocol utilizing a first strand synthesis kit obtained from CLON-TECH (Palo Alto, Calif.). The purity of the cDNA was evaluated by PCR using primers specific for the p53 gene. These primers span an intron such that pure cDNA can be distinguished from cDNA that is contaminated with genomic DNA.

EXAMPLE 3

PCR with Redundant Primers, Cloning of TADG-15 cDNA. T-Vector Ligation and Transformations and DNA Sequencing Redundant Primers,
forward 5'-TGGGTIGTIACIGCIGCICA(C/T)TG-3' (SEQ ID No. 11) and reverse 5'-A(A/G)IGGICCICCI (C/G)(T/A)(A/G)TCICC-3' (SEQ ID No. 12), corresponding to the amino acids surrounding the catalytic triad for serine proteases, were used to compare the PCR products from normal and carcinoma cDNAs.

The purified PCR products were ligated into the Promega T-vector plasmid and the ligation products used to transform JM109 competent cells according to the manufacturer's instructions (Promega). Positive colonies were cultured for amplification, the plasmid DNA isolated using the Wizard™ Minipreps DNA purification system (Promega), and the plasmids were digested with ApaI and SacI restriction enzymes to determine the size of the insert. Plasmids with inserts of the size(s) visualized by the previously described PCR product gel electrophoresis were sequenced.

Individual colonies were cultured and plasmid DNA was isolated using the Wizard Miniprep DNA purification system (Promega). Applied Biosystems Model 373A DNA sequencing system was used for direct cDNA sequence determination. Utilizing a plasmid-specific primer near the cloning site, sequencing reactions were carried out using PRISM™ Ready Reaction Dye Deoxy™ terminators (Applied Biosystems) according to the manufacturer's instructions. Residual dye terminators were removed from the completed sequencing reaction using a Centri-sep™ spin column (Princeton Separation). Based upon the determined sequence, primers that specifically amplify the gene of interest were designed and synthesized.

The original TADG-15 subclone (436 bp) was randomly labeled and used as a probe to screen an ovarian tumor cDNA library by standard hybridization techniques.[13] The library was constructed in 8ZAP using mRNA isolated from the tumor cells of a stage III/grade III ovarian adenocarcinoma patient. Three overlapping clones were obtained which spanned 3147 nucleotides.

EXAMPLE 4

Northern Blot Analysis

10 μg mRNAs were size separated by electrophoresis through a 1% formaldehyde-agarose gel in 0.02 M MOPS, 0.05 M sodium acetate (pH 7.0), and 0.001 M EDTA. The mRNAs were then blotted to Hybond-N$^+$ nylon membrane (Amersham) by capillary action in 20×SSPE. The RNAs are fixed to the membrane by baking for 2 hours at 80° C. $^{32}$P-labeled cDNA probes were made by Prime-a-Gene Labeling System (Promega). The PCR products amplified by the same primers described above were used for probes. The blots were prehybridized for 30 min and hybridized for 60 min at 68° C. with $^{32}$P-labeled cDNA probe in ExpressHyb Hybridization Solution (CLONTECH). Control hybridization to determine relative gel loading was performed with a β-tubulin probe.

Normal human tissues; spleen, thymus, prostate, testis, ovary, small intestine, colon and peripheral blood leukocyte, and normal human fetal tissues; brain, lung, liver and kidney (Human Multiple Tissue Northern Blot; CLONTECH) were also examined by the same hybridization procedure. Additional multiple tissue northern (MTN) blots from CLONTECH include the Human MTN blot, the Human MTN II blot, the Human Fetal MTN II blot, and the Human Brain MTN III blot.

EXAMPLE 5

Western Blot Analysis

Polyclonal rabbit antibody was generated by immunization with a poly-lysine linked multiple Ag peptide derived from the TADG-15 protein sequence 'LFRDWIKENTGV' (SEQ ID No. 13). Approximately 20 μg of cell lysates were separated on a 15% SDS-PAGE gel and electroblotted to PVDF at 100 V for 40 Min at 4° C. The proteins were fixed to the membrane by incubation in 50% MeOH for 10 min. The membrane was blocked overnight in TBS (pH 7.8) containing 0.2% non-fat milk. Primary antibody was added to the membrane at a dilution of 1:100 in 0.2% milk/TBS and incubated for 2 h at room temperature. The blot was washed and incubated with a 1:3000 dilution of alkaline-phosphatase conjugated goat anti-rabbit IgG (BioRad) for 1 h at room temperature. The blot was washed and incubated with a chemiluminescent substrate before a 10 sec exposure to X-ray film for visualization.

EXAMPLE 6

Quantitative PCR

The mRNA overexpression of TADG-15 was determined using a quantitative PCR. Quantitative PCR was performed.[11,12] Oligonucleotide primers were used for TADG-15:
forward 5'-ATGACAGAGGATTCAGGTAC-3' (SEQ ID No. 14) and
reverse 5'-GAAGGTGAAGTCATTGAAGA-3' (SEQ ID No. 15); and and for β-tubulin:
forward 5'-CGCATCAACGTGTACTACAA-3' (SEQ ID No. 16) and reverse 5'-TACGAGCTGGTGGACTGAGA-3' (SEQ ID No. 17).

β-tubulin was utilized as an internal control.

The PCR reaction mixture consists of cDNA derived from 50 ng of mRNA, 5 pmol of sense and antisense primers for both the TADG-15 gene and the β-tubulin gene, 200 μmol of dNTPs, 5 μCi of α-$^{32}$PdCTP and 0.25 units of Taq DNA polymerase with reaction buffer (Promega) in a final volume of 25 μl. The target sequences were amplified in parallel with the β-tubulin gene. Thirty cycles of PCR were carried out in a Thermal Cycler (Perkin Elmer Gene Amp 2400; Perkin-Elmer Cetus). Each cycle of PCR included 30 sec of denaturation at 94° C., 30 sec of annealing at 60° C. and 30 sec of extension at 72° C. The annealing temperature varies according to the primers that are used in the PCR reaction. For the reactions involving degenerate primers, an annealing temperature of 48° C. was used. The appropriate annealing temperature for the TADG-15- and β-tubulin-specific primers is 62° C.

A portion of the PCR products were separated on 2% agarose gels and the radioactivity of each PCR product was determined by using a PhosphoImager (Molecular Dynamics). In the present study, the expression ratio (TADG-15/β-tubulin) was used to evaluate gene expression and defined the value at mean ±2SD of normal ovary as the cut-off value to determine overexpression. The student's t test was used for comparison of the mean values of normal ovary and tumors.

EXAMPLE 7

Immunohistochemistry

Immunohistochemical staining was performed using a Vectastain Elite ABC Kit (Vector). Formalin-fixed and paraffin-embedded specimens were routinely deparaffinized and processed using microwave heat treatment in 0.01 M sodium citrate buffer (pH 6.0). The specimens were incubated with normal goat serum in a moist chamber for 30 min. After incubation with biotinylated anti-rabbit IgG for 30 min, the sections were then incubated with ABC reagent (Vector) for 30 min. The final products were visualized using the AEC substrate system (DAKO) and sections were counterstained with hematoxylin before mounting. Negative controls were performed using normal serum instead of the primary antibody.

EXAMPLE 8

Antisense TADG-15

TADG-15 is cloned and expressed in the opposite orientation such that an antisense RNA molecule (SEQ ID No. 18) is produced. For example, the antisense RNA is used to hybridize to the complementary RNA in the cell and thereby inhibit translation of TADG-15 RNA into protein.

EXAMPLE 9

Peptide Ranking

For vaccine or immune stimulation, individual 9-mers to 11-mers were examined to rank the binding of individual peptides to the top 8 haplotypes in the general population (Parker et al., (1994)). The computer program used for this analysis can be found at http://www.bimas.dcrt.nih.gov/molbio/hla_bind/. Table 1 shows the peptide ranking based upon the predicted half-life of each peptide's binding to a particular HLA allele. A larger half-life indicates a stronger association with that peptide and the particular HLA molecule. The TADG-15 peptides that strongly bind to an HLA allele are putative immunogens, and are used to inoculate an individual against TADG-15.

TABLE 1

TADG-15 peptide ranking

| HLA Type & Ranking | Start | Peptide | Predicted Dissociation$_{1/2}$ | SEQ ID No. |
|---|---|---|---|---|
| HLA A0201 | | | | |
| 1 | 68 | VLLGIGFLV | 2537.396 | 19 |
| 2 | 126 | LLYSGVPFL | 1470.075 | 20 |
| 3 | 644 | SLISPNWLV | 521.640 | 21 |
| 4 | 379 | KVSFKFFYL | 396.525 | 22 |
| 5 | 386 | YLLEPGVPA | 346.677 | 23 |
| 6 | 257 | SLTFRSFDL | 123.902 | 24 |
| 7 | 762 | ILQKGEIRV | 118.238 | 25 |
| 8 | 841 | RLPLFRDWI | 106.842 | 26 |
| 9 | 64 | GLLLVLLGI | 88.783 | 27 |
| 10 | 57 | VLAAVLIGL | 83.527 | 28 |
| HLA A0205 | | | | |
| 1 | 67 | LVLLGIGFL | 142.800 | 29 |
| 2 | 379 | KVSFKFFYL | 100.800 | 30 |
| 3 | 126 | LLYSGVPFL | 71.400 | 31 |
| 4 | 88 | KVFNGYMRI | 36.000 | 32 |
| 5 | 670 | TQWTAFLGL | 33.600 | 33 |
| 6 | 119 | KVKDALKLL | 25.200 | 34 |
| 7 | 60 | AVLIGLLLV | 24.000 | 35 |
| 8 | 62 | LIGLLLVLL | 23.800 | 36 |
| 9 | 57 | VLAAVLIGL | 23.800 | 37 |
| 10 | 61 | VLIGLLLVL | 23.800 | 38 |
| HLA A1 | | | | |
| 1 | 146 | FSEGSVIAY | 337.500 | 39 |
| 2 | 658 | YIDDRGFRY | 125.000 | 40 |
| 3 | 449 | SSDPCPGQF | 75.000 | 41 |
| 4 | 401 | YVEINGEKY | 45.000 | 42 |
| 5 | 387 | LLEPGVPAG | 18.000 | 43 |
| 6 | 553 | GSDEASCPK | 15.000 | 44 |
| 7 | 97 | TNENFVDAY | 11.250 | 45 |
| 8 | 110 | STEFVSLAS | 11.250 | 46 |
| 9 | 811 | SVEADGRIF | 9.000 | 47 |
| 10 | 666 | YSDPTQWTA | 7.500 | 48 |
| HLA A24 | | | | |
| 1 | 709 | DYDIALLEL | 220.000 | 49 |
| 2 | 408 | KYCGERSQF | 200.000 | 50 |
| 3 | 754 | QYGGTGALI | 50.000 | 51 |
| 4 | 153 | AYYWSEFSI | 50.000 | 52 |
| 5 | 722 | EYSSMVRPI | 50.000 | 53 |
| 6 | 326 | GFEATFFQL | 36.000 | 54 |
| 7 | 304 | TFHSSQNVL | 24.000 | 55 |
| 8 | 707 | TFDYDIALL | 20.000 | 56 |
| 9 | 21 | KYNSRHEKV | 16.500 | 57 |
| 10 | 665 | RYSDPTQWT | 14.400 | 58 |
| HLA B7 | | | | |
| 1 | 686 | APGVQERRL | 240.000 | 59 |
| 2 | 12 | GPKDFGAGL | 80.000 | 60 |
| 3 | 668 | DPTQWTAFL | 80.000 | 61 |
| 4 | 461 | TGRCIRKEL | 60.000 | 62 |
| 5 | 59 | AAVLIGLLL | 36.000 | 63 |
| 6 | 379 | KVSFKFFYL | 20.000 | 64 |
| 7 | 119 | KVKDALKLL | 20.000 | 65 |
| 8 | 780 | LPQQITPRM | 20.000 | 66 |
| 9 | 67 | LVLLGIGFL | 20.000 | 67 |
| 10 | 283 | SPMEPHALV | 18.000 | 68 |
| HLA B8 | | | | |
| 1 | 12 | GPKDFGAGL | 24.000 | 69 |
| 2 | 257 | SLTFRSFDL | 8.000 | 70 |
| 3 | 180 | MLPPRARSL | 8.000 | 71 |
| 4 | 217 | GLHARGVEL | 8.000 | 72 |
| 5 | 173 | MAEERVVML | 4.800 | 73 |

TABLE 1-continued

TADG-15 peptide ranking

| HLA Type & Ranking | Start | Peptide | Predicted Dissociation$_{1/2}$ | SEQ ID No. |
|---|---|---|---|---|
| 6 | 267 | SCDERGSDL | 4.800 | 74 |
| 7 | 567 | CTKHTYRCL | 4.000 | 75 |
| 8 | 724 | SSMVRPICL | 4.000 | 76 |
| 9 | 409 | YCGERSQFV | 3.600 | 77 |
| 10 | 495 | TCKNKFCKP | 3.200 | 78 |
| HLA B2702 | | | | |
| 1 | 427 | VRFHSDQSY | 1000.000 | 79 |
| 2 | 695 | KRIISHPFF | 600.000 | 80 |
| 3 | 664 | FRYSDPTQW | 500.000 | 81 |
| 4 | 220 | ARGVELMRF | 200.000 | 82 |
| 5 | 492 | HQFTCKNKF | 100.000 | 83 |
| 6 | 53 | GRWVVLAAV | 100.000 | 84 |
| 7 | 248 | LRGDADSVL | 60.000 | 85 |
| 8 | 572 | YRCLNGLCL | 60.000 | 86 |
| 9 | 692 | RRLKRIISH | 60.000 | 87 |
| 10 | 24 | SRHEKVNGL | 60.000 | 88 |
| HLA B4403 | | | | |
| 1 | 147 | SEGSVIAYY | 360.000 | 89 |
| 2 | 715 | LELEKPAEY | 360.000 | 90 |
| 3 | 105 | YENSNSTEF | 60.000 | 91 |
| 4 | 14 | KDFGAGLKY | 50.625 | 92 |
| 5 | 129 | SGVPFLGPY | 36.000 | 93 |
| 6 | 436 | TDTGFLAEY | 33.750 | 94 |
| 7 | 766 | GEIRVINQT | 30.000 | 95 |
| 8 | 402 | VEINGEKYC | 30.000 | 96 |
| 9 | 482 | DELNCSCDA | 24.000 | 97 |
| 10 | 82 | RDVRVQKVF | 22.500 | 98 |

EXAMPLE 10

TADG-15 cDNA

A screening strategy to identify proteases which are overexpressed in human cancer has been developed in which RT-PCR products amplified specifically in tumors, as compared to normal tissue, are examined.[9] During this effort, candidate genes were identified using redundant sense primers to the conserved amino acid histidine domain at the NH$_3$ end of the catalytic domain and antisense primers to the downstream conserved amino acid serine domain. Subcloning and sequencing the appropriate 480 base pair band(s) amplified in such a PCR reaction provides the basis for identifying the gene(s) encoding proteases(s). Among these amplified catalytic domains, a new serine protease gene named TADG-15 (tumor antigen-derived gene 15) was identified. The catalytic domain of the newly identified TADG-15 protein is similar to other serine proteases and specifically contains conserved amino acids appropriate for the catalytic domain of the trypsin-like serine protease family.

A computerized search of GenEMBL databases using the FASTA program (Wisconsin Package Version 9.1, GCG, Madison, Wis.) for amino acid sequences homologous to the TADG-15 protease domain revealed that homologies with other known human proteases never exceeds 55%. FIGS. 1A and 1B show the alignment of the protease domain of TADG-15 compared with other human serine proteases. Using the BESTFIT program, available through GCG, the similarities between TADG-15 and trypsin, chymotrypsin, and tissue-type plasminogen activator are 51%, 46% and 52%, respectively.

From the sequence derived from the TADG-15 catalytic domain, specific primers were synthesized to amplify a TADG-15-specific probe for library screening. After screening an ovarian carcinoma library, one 1785 bp clone was obtained which included the 3"end of the TADG-15 transcript. Upon further screening using the 5"end of the newly detected clone, two additional clones were identified which provided another 1362 bp of the cDNA, including the 5' end of the TADG-15 transcript. The total length of the sequenced cDNA was approximately 3.15 kb. The total nucleotide sequence obtained includes a Kozak's consensus sequence preceding a single open reading frame encoding a predicted protein of 855 amino acids (FIGS. 2A–2D).

The deduced open reading frame encoded by the TADG-15 nucleotide sequence (FIGS. 2A–2D, 3 and 4) contains several distinct domains as follows: an amino terminal cytoplasmic tail (amino acids (aa) #1–54), a potential transmembrane domain (aa #55–77), an extracellular membrane domain (aa #78–213), two complement subcomponents Clr/Cls, Uegf, and bone morphogenetic protein 1 (CUB) repeats (aa #214–447), four ligand binding repeats of the low density lipoprotein (LDL) receptor-like domain (aa #453–602) and a serine protease domain (aa #615–855). The TADG-15 protein also contains two potential N-linked glycosylation sites (aa #109 and 302) and a potential proteolytic cleavage site upstream from the protease domain (aa #614) which could release and/or activate the protease at the carboxy end of this protein. In, addition, TADG-15 contains an RGD motif (aa #249–251) which is commonly found in proteins involved in cell—cell adhesion.

EXAMPLE 11

TADG-15 Expression

Figure 5:
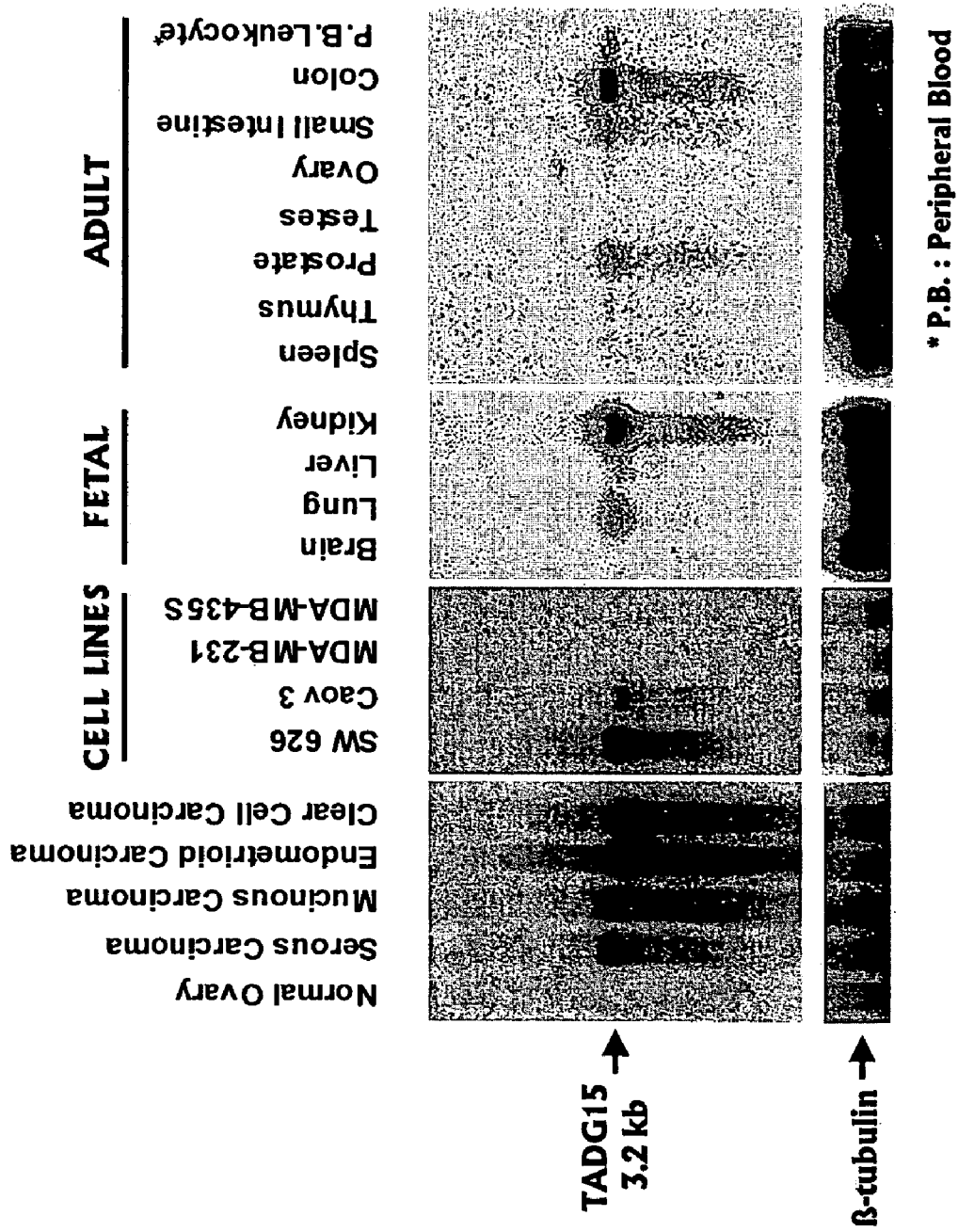
FIG. 5 shows Northern blot analysis of TADG-15 mRNA expression in normal ovary, ovarian carcinomas, carcinoma cell lines, normal fetal tissues and normal adult tissues. A single intense transcript of the TADG-15 was observed in every sub-type of carcinoma and the two ovarian carcinoma cell lines, SW626 and CAOV3, whereas no visible band was detected in normal ovary or the two breast cancer cell lines. In normal fetal tissues, fetal kidney showed increased transcript and faint expression was detected in fetal lung. In normal adult tissues, the TADG-15 was detected in colon with low expression in small intestine and prostate.

To examine the size of the transcript for TADG-15 and its pattern of expression in various tissues, Northern blot hybridization was performed for representative histological types of carcinoma and in a series of cell lines, fetal tissues and normal adult tissues (FIG. 5). The transcript size for the TADG-15 message was determined to be approximately 3.2 kb and a single intense transcript appeared to be present in all of the carcinomas examined, whereas no visible band was detected in normal ovary (FIG. 5). This transcript size is also in good agreement with the sequence data predicting a transcript size of 3.15 kb. The ovarian tumor cell lines, SW626 and CAOV3, also showed an abundance of transcript, however little or no transcript was detectable in the breast carcinoma cell lines MDA-MB-231 and MDA-MB-4355. Among normal human fetal tissues, fetal kidney showed an abundance of the TADG-15 transcript and low expression was also detected in fetal lung. In normal adult tissues, TADG-15 was detected in colon with low levels of expression in small intestine and prostate (FIG. 5).

Figure 6A:
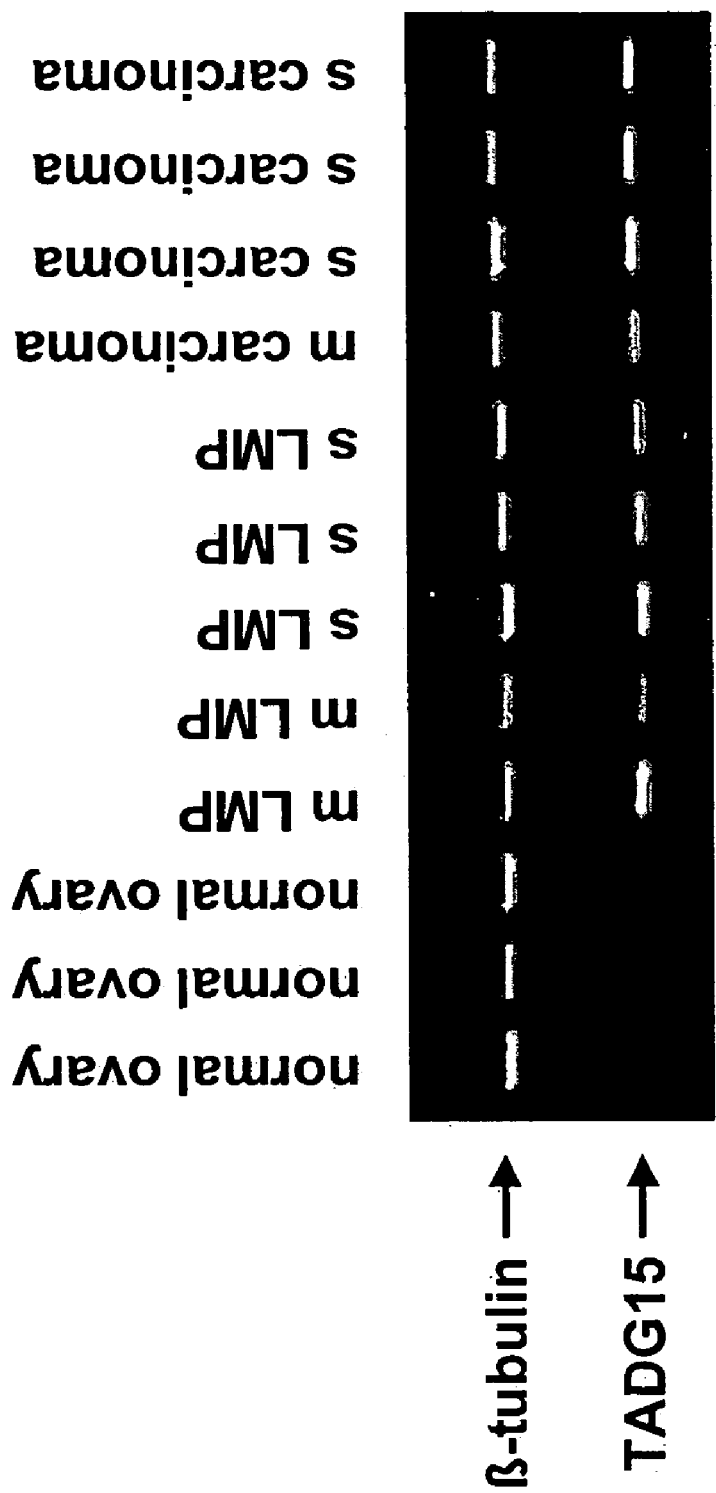
FIG. 6A shows quantitative PCR analysis of TADG-15 expression. Expression levels of TADG-15 relative to β-tubulin are significantly elevated in all LMP tumors and carcinomas compared to that of normal ovaries. m; mucinous, s; serous.

To evaluate mRNA transcript expression of TADG-15 in ovarian tumors and normal ovary, semi-quantitative PCR (FIG. 6) was performed. In a preliminary study, the linearity of this assay[11,12] was confirmed and its efficacy correlated with both Northern blots and immunohistochemistry. The data was quantified using a phosphoimager and compared as a ratio of expression (TADG-15/β-tubulin). Results herein indicate that TADG-15 transcript expression is elevated above the cut-off value (mean for normal ovary±2 SD) in all of the tumor cases examined and is either not detected or detected at extremely low levels in normal ovaries (FIGS. 6A and B). Analysis of ovarian carcinoma subtypes, including early stage and late stage disease, confirms overexpression of TADG- 15 in all carcinomas examined (Table 2). All of the carcinomas studied, which included 5 stage I and 3 stage II carcinomas, showed overexpression of the TADG-15 gene.

These data can also be examined with regard to tumor stage and histological sub-type, and results indicated that every carcinoma of every stage and histological sub-type overexpressed the TADG-15 gene. The expression ratio (mean value±SD) for normal ovary group was determined as, 0.182±0.024, for LMP tumor group as 0.847±0.419 and for carcinoma group as 0.771±0.380 (Table 2). A comparison between the normal ovary group and tumor groups showed that overexpression of the TADG-15 gene is statistically significant in both the LMP tumor group and the carcinoma group (LMP tumor: p<0.001, carcinoma: p<0.0001).

Figure 6B:
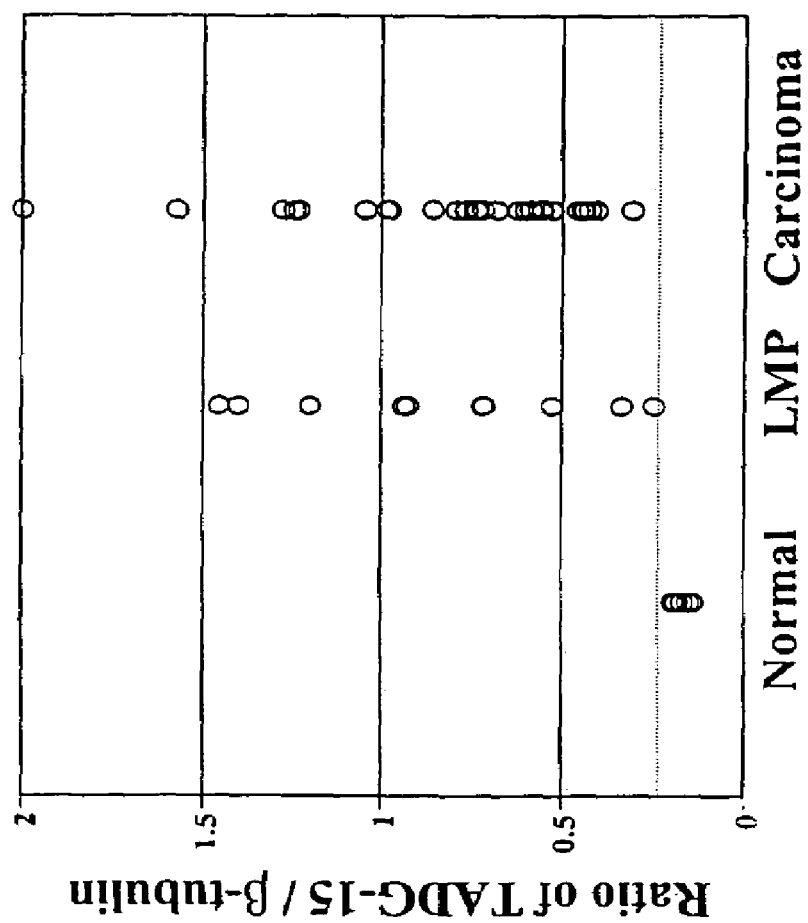
FIG. 6B shows the ratio of TADG-15 expression to expression of β-tubulin in normal ovary, LMP tumor and ovarian carcinoma. TADG-15 mRNA expression levels were significantly elevated in both LMP tumor (*; p<0.001) and carcinoma (**; p<0.0001) compared to that in normal ovary. All 10 samples of normal ovary showed a low level of TADG-15 expression.
Figure 7:
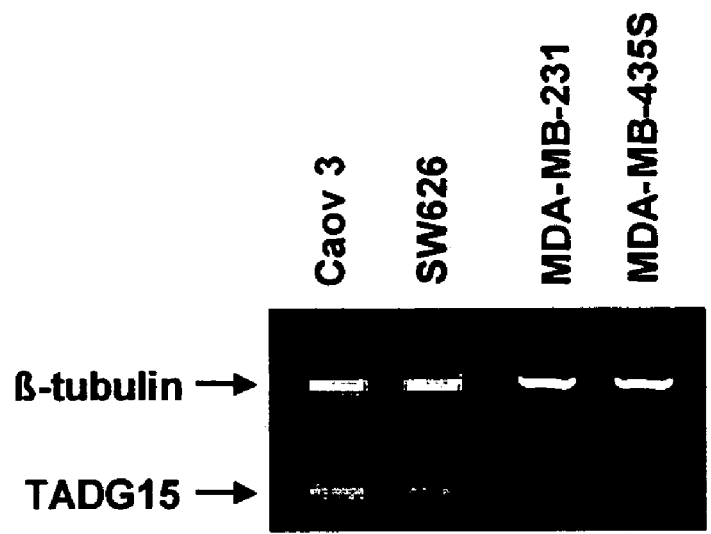
FIG. 7 shows the TADG-15 expression in tumor cell lines derived from both ovarian and breast carcinoma tissues.
Figure 8:
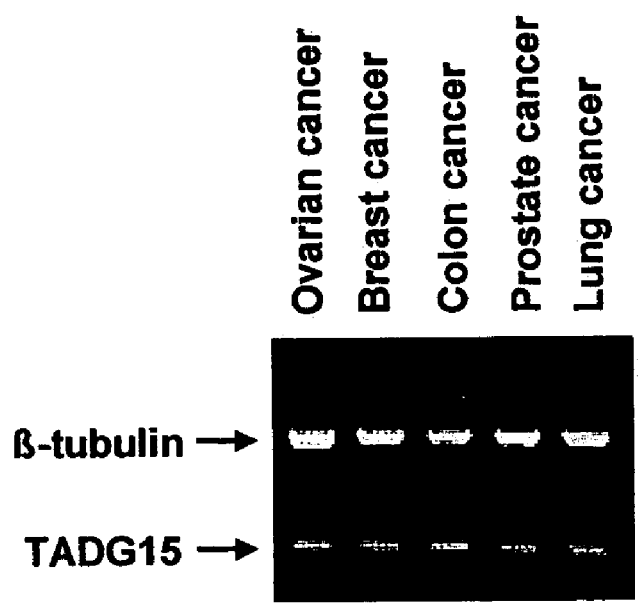
FIG. 8 shows the overexpression of TADG-15 in other tumor tissues.

As shown in FIG. 6, TADG-15 transcripts were noted in all ovarian carcinomas, but were not present at detectable levels in any of the following tissues: a) normal ovary, b) fetal liver and brain, c) adult spleen, thymus, testes, ovary and peripheral blood lymphocytes, d) skeletal muscle, liver, brain or heart. This evaluation was extended to a standard panel of about 40 tumors. Using TADG-15-specific primers, the expression was also examined in tumor cell lines derived from both ovarian and breast carcinoma tissues as shown in FIG. 7 and in other tumor tissues as shown in FIG. 8. Expression of TADG-15 was also observed in carcinomas of the breast, colon, prostate and lung.

Figure 9:
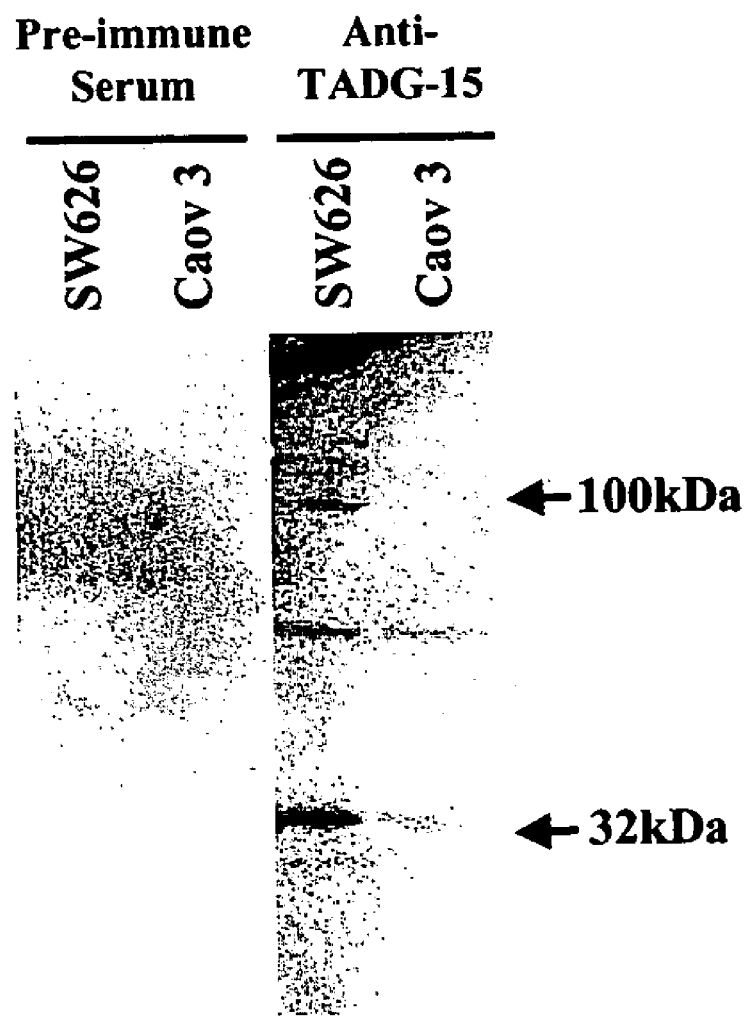
FIG. 9 shows SW626 and CAOV3 cell lysates that were separated by SDS-PAGE and immunoblotted. Lanes 1 and 2 were probed with rabbit pre-immune serum as a negative control. Lanes 3 and 4 were probed with polyclonal rabbit antibody generated to a carboxy terminal peptide from TADG-15 protein sequence.

Polyclonal antibodies developed to a synthetic peptide (a 12-mer) at the carboxy terminus of the protease domain were used to examine TADG-15 expression in cell lines by Western blot and by immunolocalization in normal ovary and ovarian tumors. Western blots of cell extracts from SW626 and CAOV3 cells were probed with both antibody and preimmune sera (FIG. 9). Several bands were detected with the antibody, including bands of approximately 100,000 daltons, approximately 60,000 daltons and 32,000 daltons. The anticipated molecular size of the complete TADG-15 molecule is estimated to be approximately 100,000 daltons, and the protease domain which may be released by proteolytic cleavage at aa #614 is estimated to be approximately 32,000 daltons. Some intermediate proteolytic product may be represented by the 60,000 dalton band.

Antibody staining of tumor cells confirms the presence of TADG-15 protease in the cytoplasm of a serous LMP tumor, mucinous LMP tumor and serous carcinoma (FIG. 10B, C & D, respectively). This diffuse staining pattern may be due to detection of TADG15 within the cell as it is being packaged and transported to the cell surface. In endometrioid carcinoma, the antigen is clearly detectable on the surface of tumor cells (FIG. 10E). No staining was detected in normal ovarian epithelium or stromal cells (FIG. 10A). Immunohistochemical staining of a series of 27 tumors indicates the presence of the TADG-15 protein in all the carcinoma subtypes examined, including the low malignant potential group. Strong staining was noted in 7 of 9 low malignant potential tumors and 13 of 18 carcinomas (Table 3).

Table 2

Number of Cases with Overexpression of TADG-15 in Normal Ovaries and Ovarian Tumors

TABLE 2

Number of cases with overexpression of TADG-15 in normal ovaries and ovarian tumors

|  | N | overexpression of TADG-15 | expression ratio[a] |
|---|---|---|---|
| Normal | 10 | 0 (0%) | 0.182 ± 0.024 |
| LMP | 10 | 10 (100%) | 0.847 ± 0.419 |
| serous | 6 | 6 (100%) | 0.862 ± 0.419 |
| mucinous | 4 | 4 (100%) | 0.825 ± 0.483 |
| Carcinoma | 31 | 31 (100%) | 0.771 ± 0.380 |
| serous | 18 | 18 (100%) | 0.779 ± 0.332 |
| mucinous | 7 | 7 (100%) | 0.907 ± 0.584 |
| endometrioid | 3 | 3 (100%) | 0.502 ± 0.083 |
| clear cell | 3 | 3 (100%) | 0.672 ± 0.077 |

[a]The ratio of expression level of TADG-15 to β-tubulin (mean ± SD)

TABLE 3

Immunohistochemical staining using TADG-15

| Lab No. | Histology | TADG-15 |
|---|---|---|
|  | Surface epithelium of the ovary | − |
| H-3194 | serous (LMP) | ++ |
| H-162 | serous (LMP) | ++ |
| H-1182 | serous (LMP) | ++ |
| H-4818 | serous (LMP) | ++ |
| H-4881 | serous (LMP) | ++ |
| H-675 | mucinous (LMP) | + |
| H-2446 | mucinous (LMP) | + |
| H-0707 | mucinous (LMP) | ++ |
| H-2042 | mucinous (LMP) | ++ |
| H-2555 | serous carcinoma | ++ |
| H-1858 | serous carcinoma | ++ |
| H-5266 | serous carcinoma | ++ |
| H-5316 | serous carcinoma | + |
| H-2597 | serous carcinoma | + |
| H-4931 | mucinous carcinoma | ++ |
| H-1867 | mucinous carcinoma | ++ |
| H-5998 | mucinous carcinoma | ++ |
| H-2679 | endometrioid adenocarcinoma | + |
| H-5718 | endometrioid adenocarcinoma | ++ |
| H-3993 | endometrioid adenocarcinoma | + |
| H-2991 | endometrioid adenocarcinoma | ++ |
| H-2489 | endometrioid adenocarcinoma | ++ |
| H-5994 | clear cell carcinoma | ++ |
| H-6718 | clear cell carcinoma | ++ |
| H-1661 | clear cell carcinoma | ++ |
| H-6201 | clear cell carcinoma | ++ |
| H-5640 | clear cell carcinoma | + |

− Negative; + Weak Positive; ++ Strong Positive (more than 50% of cell staining)

EXAMPLE 12

TADG-15 Homology

Recently, a mouse protein named epithin (GenBank Accession No. AF04282) has been described.[14] Epithin is a 902 amino acid protein which contains a similar structure to TADG-15 in that it has a cytoplasmic domain, transmembrane domain, two CUB domains, four LDLR-like domains and a carboxy terminal serine protease domain. TADG-15 and epithin are 84% similar over 843 amino acids, suggesting that the proteins may be orthologous (FIGS. 11A and 11B). The precise role of epithin remains to be elucidated.

A search of GeneBank for similar previously identified sequences yielded one such sequence with relatively high homology to a portion of TADG-15 from nucleotide #182 to 3139 and SNC-19 GeneBank Accession No. #U20428) is approximately 97% (FIGS. 12A–12E). There are however significant differences between SNC-19 and TADG-15. For example, TADG-15 has an open reading frame of 855 amino acids whereas the longest open reading frame of SNC-19 is 173 amino acids. Additionally, SNC-19 does not include a proper start site for the initiation of translation, nor does it include the amino terminal portion of the protein encoded by TADG-15. Moreover, SNC-19 does not include an open reading frame for a functional serine protease because the His, Asp and Ser residues of the catalytic triad that are necessary for function are encoded in different reading frames.

Implications

The overall structure of the TADG-15 protein is relatively similar to the members of the tolloid/BMP-1 family and the complement subcomponents, Clr/Cls. These proteins contain both CUB and protease domains, and complex formation through the ligand binding domain is essential for their function. Activation of the serine protease domains of Clr and Cls requires proteolytic cleavage of Arg-Gly and Arg-Ile bonds, respectively.[15] Similarly, it might be expected that the TADG-15 protein is synthesized as a zymogen, which is activated by cleavage between Arg$^{614}$ and Val$^{615}$ and analogous to the activation mechanism of other serine protease zymogens. Western blot analysis of cultured cell lysates confirmed both a 100 kDa and 32 kDa peptide, which correspond to the putative zymogen (whole molecule) and a cleaved protease product of TADG-15 (FIG. 9). These data support a model for proteolytic release and/or activation of TADG-15 as occurs for similar type II serine proteases.

CUB domains were first found in complement subcomponents Clr/Cls[16-18] and are known to be a widespread module in developmentally regulated proteins, such as the bone morphogenetic protein-1 (BMP-1) and the tolloid gene product.[18-20] The role of these repeats remains largely unknown. However, some models suggest that the CUB domain may be involved in protein—protein interactions. The CUB domain of Clr and Cls participates in the assembly of the Cls-Clr-Clr-Cls tetrameric complex in the activation of the classical pathway of complement by providing protein—protein interaction domains.[15] The *Drosophila* decapentaplegic (DPP) protein is essential for dorsal-ventral specification of the embryo, and the *Drosophila* tolloid (TLD) forms a complex with DPP to regulate its activity.[19-20] Missense mutations in the CUB domain of the tolloid protein results in a phenotype that does not allow a protein interaction with the DPP complex.[19]

The TADG-15 protein contains two tandem repeats of CUB-like domains between amino acid residues 214 and 447. Each of these is approximately 110 amino acids long and each has four conserved cysteine residues characteristic of other CUBs (amino acids 214, 244, 268, 294, 340, 366, 397, 410). By analogy, the CUB repeats of the TADG-15 protein may form an interactive domain capable of promoting multimeric complex formation and regulating the activity of the target protein or TADG-15 itself.

The TADG-15 protein also contains the LDL receptor ligand binding repeat (class A motif)-like domain, which consists of four contiguous cysteine-rich repeats (amino acid residues 453 to 602). Each cysteine-rich repeat is approximately 40 amino acids long and contains a conserved, negatively-charged sequence (Ser-Asp-Glu) with six cysteine residues. In the LDL receptor protein, this repeat is thought to function as a protein-binding domain which interacts with the lysine and arginine residues present in lipoproteins.[21,22] In addition, the first repeat of the LDL receptor appears to bind $Ca^{2+}$ and not the lipoproteins.[23] By analogy, it is possible that the LDL receptor-like repeat in TADG-15 may act in a similar fashion, interacting with positively charged regions of other proteins and/or as a $Ca^{2+}$ binding site. As a result of ligand binding and the formation of receptor-ligand complex, LDL receptor is internalized via clathrin-coated pits.[24] These types of plasma membrane receptors contain a characteristic amino acid sequence in their cytoplasmic domain for binding to clathrin-coated pits.[24] TADG-15 does not contain this motif in its cytosolic region, and furthermore, no similarities with other known protein sequences were found in the cytoplasmic domain of the TADG-15. This finding suggests that TADG-15 functions in a different manner from the endocytic receptors (such as the LDL receptor), although TADG-15 possesses similar ligand-binding repeats in the extracellular matrix.

Although the precise role of TADG-15 is unknown, this gene is clearly overexpressed in ovarian tumors. A variety of proteases, such as type IV collagenase and plasminogen activator, appear to be involved in the process of tumor invasion and are constituents of a protease cascade in malignant progression. TADG-15 may constitute such an activity and directly digest extracellular matrix components surrounding a tumor, or activate other proteases by cleavage of inactive precursors, indirectly enhancing tumor growth and invasion. It is also possible that TADG-15 may function like a member of the tolloid/BMP-1 family by forming complexes with other growth factors or signal transduction proteins to modulate their activities.

These data raise the possibility that the TADG-15 gene and its translated protein will be a useful marker for the early detection of ovarian carcinoma through release of the protease domain into the extracellular matrix and ultimately the circulation. These data also suggest the possibility of using TADG-15 as a target for therapeutic intervention through delivery systems directed at the CUB/LDLR ligand binding domains.

The following references were cited herein:
1. Liotta, L. A., et al. Cell, 64: 327–336, 1991.
2. Duffy, M. J. Clin. Exp. Metastasis, 10: 145–155, 1992.
3. Tryggvason, K., et al. Biochem. Biophys. Acta., 907: 191–217, 1987.
4. Levy, A. T., et al. Cancer Res., 51: 439–444, 1991.
5. Monsky, W. L. et al. Cancer Res., 53: 3159–3164, 1993.
6. Duffy, M. J. et al. Cancer, 62: 531–533, 1988.
7. Hackel, C., et al. Cancer, 79: 53–58, 1997.
8. Watt, K, et al. Proc. Natl. Acad. Sci. U.S.A., 83: 3166–3170, 1986.
9. Tanimoto, H. et al. Cancer Res., 57: 2884–2887, 1997.
11. Shigemasa,. K. et al. J. Soc. Gynecol. Invest., 4: 95–102, 1997.
12. Tanimoto, H. et al. Gynecol. Oncol., 66: 308–312, 1997.
13. Maniatis, T., Fritsch, E. F. & Sambrook, J. Molecular Cloning, p. 309–361 Cold Spring Harbor Laboratory, New York, 1982.
14. Kim, M. G., et al. Immunogenetics, 49(5): 420–428, 1999.
15. Arlaud et al. Method in Enzymology, 223: 61–82, 1993.
16. Journet, A. & Tosi, M. Biochem. J., 240: 783–787, 1986.
17. Mackinnon, C. M., et al. Eur. J. Biochem., 169: 547–553, 1987.
18. Bork, P. & Beckmann, G. J. Mol. Biol., 231: 539–545, 1993.
19. Childs, S. R. & O'Connor, M. B. Dev. Biol., 162: 209–220, 1994.
20. Blader, P L, et al. Science, 278: 1937–1940, 1997.
21. Yamamoto, T. et al. Cell, 39: 27–38, 1984.
22. Daly, N. L., et al. Proc. Natl. Acad. Sci., 92: 6334–6338, 1995.
23. van Driel, I. R., et al. J. Biol. Chem., 262: 17443–17449, 1987.

24. Lodish, H. et al. Sorting of membrane proteins internalized from the cell surface. In: Molecular Cell Biology, 3rd ed., p. 722–733 Scientific American Books, Inc., New York, 1995.
25. Parker, K C et al. J. Immunol. 152:163, 1994.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A kit for detecting a Tumor Antigen Derived Gene-15 (TADG-15) protein, which is SEQ ID No. 2, comprising:
   an antibody specific for the TADG-15 protein, wherein said TADG-15 protein has a molecular size of 100 kDa and comprises CUB, LDLR and serine protease domains; and
   detectable labels to label said antibody.

2. An antibody specific for a Tumor Antigen Derived Gene-15 (TADG-15) protein, which is SEQ ID No. 2, wherein said TADG-15 protein has a molecular size of 100 kDa and comprises CUB, LDLR and serine protease domains.

3. A kit for detecting a Tumor Antigen Derived Gene-15 (TADG-15) protein, comprising:
   an antibody specific for the TADG-15 protein, wherein said TADG-15 protein has a molecular size of 100 kDa; and
   detectable labels to label said antibody.

4. An antibody specific for a Tumor Antigen Derived Gene-15 (TADG-15) protein, which is SEQ ID No. 2, wherein said TADG-15 protein has a molecular size of 100 kDa.

5. A kit for detecting a Tumor Antigen Derived Gene-15 (TADG-15) protein, which is SEQ ID No. 2, comprising:
   an antibody specific for the TADG-15 protein, wherein said TADG-15 protein comprises CUB, LDLR and serine protease domains; and
   detectable labels to label said antibody.

6. An antibody specific for a Tumor Antigen Derived Gene-15 (TADG-15) protein, which is SEQ ID No. 2, wherein said TADG-15 protein comprises CUB, LDLR and serine protease domains.

* * * * *